United States Patent [19]
Chesney et al.

[11] Patent Number: 6,132,383
[45] Date of Patent: Oct. 17, 2000

[54] APPARATUS FOR HOLDING AND POSITIONING AN ARTERIAL PULSE PRESSURE SENSOR

[75] Inventors: Charles F. Chesney, Sunfish Lake; Bernard M. Graham, Maple Grove; E. Paul Maloney, Stillwater; Dennis J. Morgan, Crystal; Andrew L. Von Duyke, Minnetonka, all of Minn.

[73] Assignee: Hypertension Diagnostics, Inc., Eagan, Minn.

[21] Appl. No.: 09/045,449

[22] Filed: Mar. 20, 1998

[51] Int. Cl.⁷ ........................................................ A61B 5/02
[52] U.S. Cl. .......................... 600/502; 600/485; 600/503; 73/700; 73/866.5
[58] Field of Search ..................................... 600/485, 490, 600/492, 493, 494, 499, 500, 502, 503, 372, 427, 439, 459, 465, 561; 73/65.09, 700, 866.5; 269/55, 56, 58

[56] References Cited

U.S. PATENT DOCUMENTS

| | | | |
|---|---|---|---|
| 3,651,353 | 3/1972 | Hugli et al. | |
| 4,409,983 | 10/1983 | Albert | 128/690 |
| 4,431,873 | 2/1984 | Dunn et al. | |

(List continued on next page.)

FOREIGN PATENT DOCUMENTS

| | | |
|---|---|---|
| 0357275A1 | 3/1990 | European Pat. Off. |
| 87/02233 | 4/1987 | WIPO |
| 92/09232 | 6/1992 | WIPO |
| 94/05207 | 3/1994 | WIPO |
| 95/06525 | 3/1995 | WIPO |

OTHER PUBLICATIONS

"Acoustic Contact Sensor", *Apollo Research Corp.*, Model 701010, 1–5, (1997).
"Aging Arteries", *Harvard Heart Letter*, 8(2), 4 pgs., (Oct. 1997).
"Guide to Modern Piezoelectric Ceramics", Advertising Material from Morgan Matroc, Inc. (undated), 6 pages.
"Harvard Heart Letter", *Harvard Medical School*, 7(7), 5 pp., (Mar. 1997).
"Nellcor's N–CAT Continuous Noninvasive Blood Pressure Monitor, Model N–500", Product Publication by Nellcor, Inc., 9 pages, (1991).
"Non–Invasive Arterial Waveform Analysis and Blood Pressure Measurement", Pulse Dynamic Oscillometrics Clinical Information, Pulse Metric, Inc., San Diego, CA, 4.
"Non–Invasive Blood Pressure/Pulse Rate Monitoring and Recording System", Portfolio™ Health Series, 6 pages.

(List continued on next page.)

*Primary Examiner*—Linda C. M. Dvorak
*Assistant Examiner*—Bryan K. Yarnell
*Attorney, Agent, or Firm*—Schwegman, Lundberg Woessner & Kluth, P.A.

[57] ABSTRACT

A sensor holding and positioning device. In one embodiment, the device includes a sensor base having two feet, the base forming a raised bridge between the two feet. The bridge has one or more cross members spanning all or part of the space between the two feet. A sensor suspension including a sensor holder and sensor-height-adjustment mechanism is coupled by a pivot-arm axle to the sensor base, such that the sensor suspension is able to rotate in an arc about the long axis of the axle. In one such embodiment, the device further includes a pressure sensor attached to the sensor holder of the sensor suspension. In another such embodiment, the sensor suspension is able to slide back and forth along a line parallel to the long axis of the axle. Another aspect is for positioning the sensor over the radial artery, for example in a human's wrist. Yet another aspect is a pulse-waveform acquisition system. In one embodiment, such a system includes a wrist stabilizer, the stabilizer comprising a first member shaped on a forearm portion to conform to contours of a forearm, shaped on a wrist portion to contours of a wrist, and shaped on a hand portion to the contours of a hand, and forming an angle of approximately 150 degrees between the forearm portion and the hand portion, the stabilizer further including straps for holding the forearm and hand to the stabilizer.

22 Claims, 19 Drawing Sheets

U.S. PATENT DOCUMENTS

| | | |
|---|---|---|
| 4,672,967 | 6/1987 | Kroll . |
| 4,784,154 | 11/1988 | Shirley et al. . |
| 4,889,133 | 12/1989 | Nelson et al. . |
| 4,947,859 | 8/1990 | Brewer et al. . |
| 4,949,710 | 8/1990 | Dorsett et al. . |
| 4,993,422 | 2/1991 | Hon et al. . |
| 5,035,247 | 7/1991 | Heimann . |
| 5,211,177 | 5/1993 | Chesney et al. . |
| 5,240,007 | 8/1993 | Pytel et al. . |
| 5,241,964 | 9/1993 | McQuilkin . |
| 5,269,312 | 12/1993 | Kawamura et al. . |
| 5,316,004 | 5/1994 | Chesney et al. . |
| 5,337,750 | 8/1994 | Walloch . |
| 5,524,637 | 6/1996 | Erickson . |
| 5,544,651 | 8/1996 | Wilk . |
| 5,551,437 | 9/1996 | Lotscher . |
| 5,551,438 | 9/1996 | Moses . |
| 5,560,366 | 10/1996 | Barada et al. . |
| 5,577,508 | 11/1996 | Medero ................................. 128/681 |
| 5,584,298 | 12/1996 | Kabal . |
| 5,590,661 | 1/1997 | Ohmori et al. . |
| 5,592,401 | 1/1997 | Kramer . |
| 5,617,868 | 4/1997 | Harada et al. . |
| 5,623,933 | 4/1997 | Amano et al. . |
| 5,638,823 | 6/1997 | Akay et al. . |
| 5,640,964 | 6/1997 | Archibald et al. . |
| 5,642,733 | 7/1997 | Archibald et al. . |
| 5,647,369 | 7/1997 | Petrucelli et al. . |
| 5,649,542 | 7/1997 | Archibald et al. . |
| 5,671,750 | 9/1997 | Shinoda . |
| 5,704,362 | 1/1998 | Hersh et al. ............................ 128/280 |
| 5,752,919 | 5/1998 | Schrimpf . |

OTHER PUBLICATIONS

Bing, et al., "Reversal of Acetylcholine Effect on Atherosclerotic Coronary Arteries by Estrogen: Pharmacologic Phenomenon of Clinical Importance?", *Journal of the American college of Cardiology,* 3 pages, (Aug. 1992).

Brinton, et al.,"Arterial Compliance by Cuff Sphygmomanometer", *Hypertension,* 28(4), Application to Hypertension and Early Changes in Subjects at Genetic Risk, 599 –603, (Oct. 1996).

Brinton, et al., "The Development and Validation of a New Non–invasive Method to Evaluate Ventricle Function During Routine Blood Pressure Monitoring", *American Journal of Hypertension,* 10(4) Part 2 (Abstract Issue), 2 pages, (1997).

Cohn, J.N., et al., "Noninvasive Pulse wave Analysis for the early detection of Vascular Disease", *Hypertension,* 26, 503–508, (Sep., 1995).

Glasser, et al., "Vascular Compliance and Cardiovascular Disease",*AJH,* 10(10), Part 1, 1175–1189, (Oct. 1997).

Kluger, J., "Beyond Cholesterol", *Time,* 48, (Aug. 4, 1997).

McVeigh, et al., "Vascular Abnormalities Associated with Long–term Cigarette Smoking Identified by Arterial Waveform Analysis", *The American Journal of Medicine,* 102, 227–231, (Mar. 1997).

Rajkumar, et al., "Hormonal Therapy Increases Arterial Compliance in Postmenopausal Women", *JACC,* 30(2), 350–356, (Aug. 1997).

Simon, et al., "Detection of Preclinical Atherosclerosis May Optimize the Management of Hypertension", *AJH,* 10(7) Part 1, 813–824, (Jul. 1997).

Yoshizawa, et al., "Classical but Effective Techniques for Estimating Cardiovascular Dynamics", *IEEE Engineering in Medicine & Biology Magazine,* 16(5), 106–112, (Sep.–Oct. 1997).

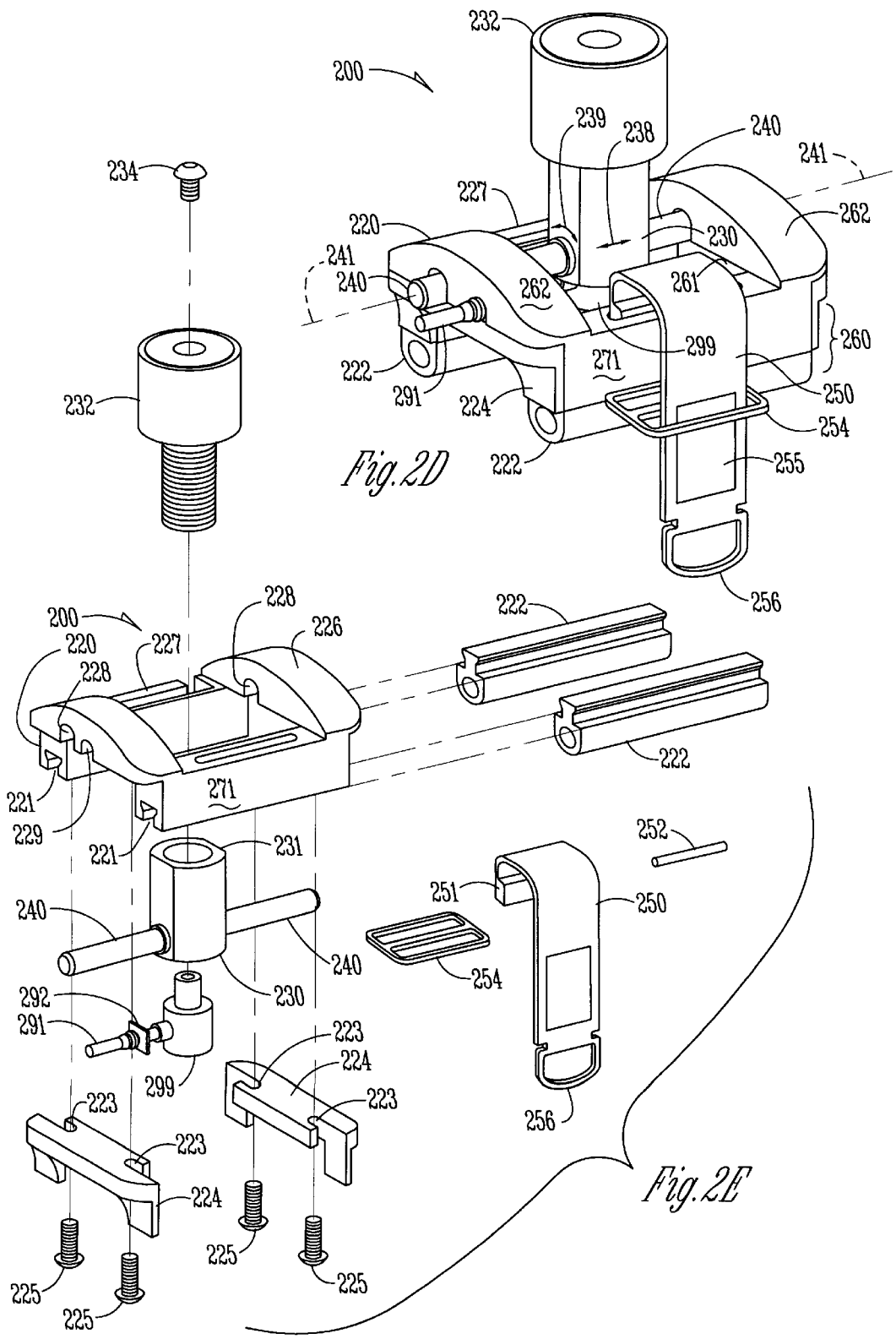

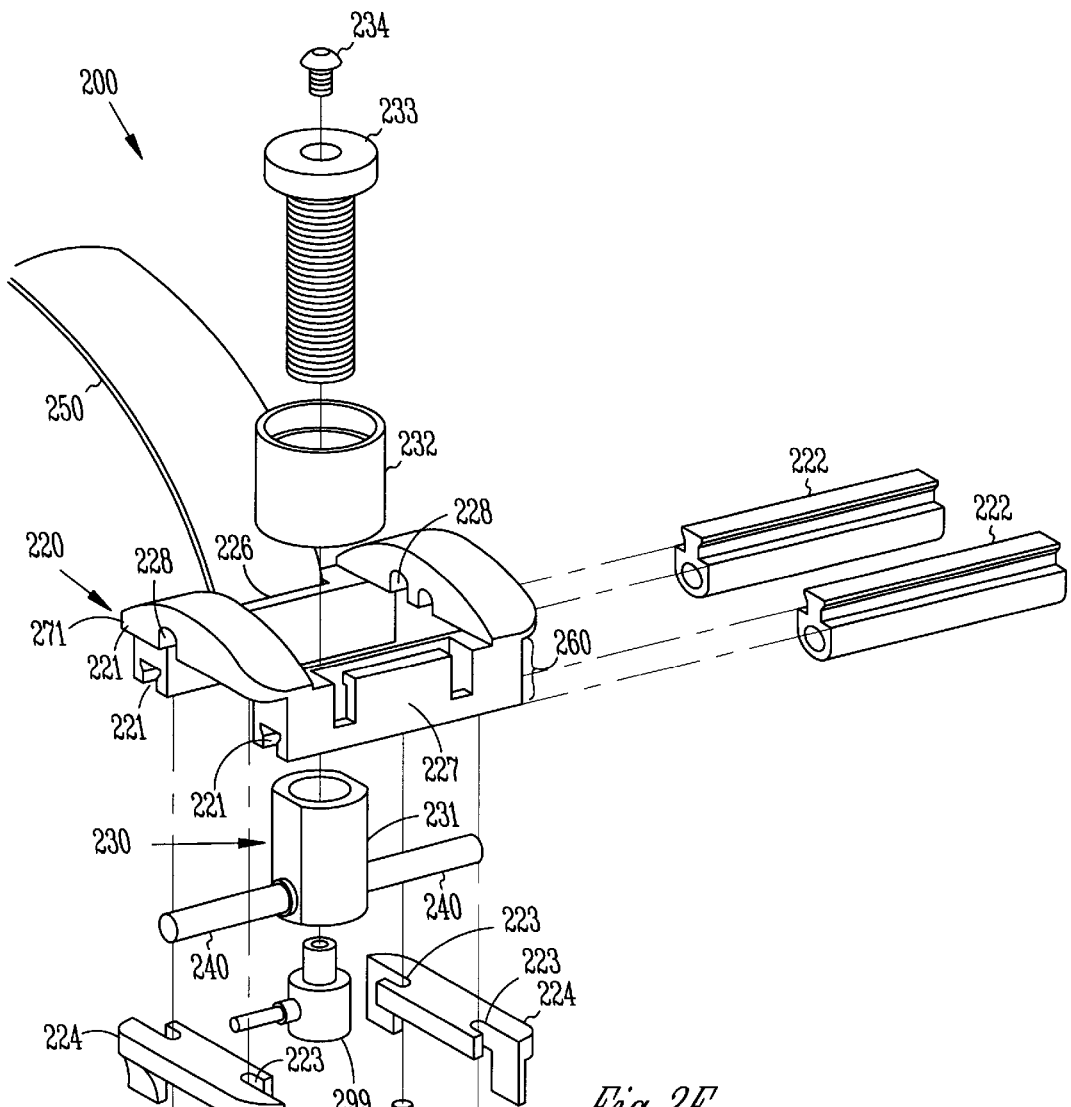
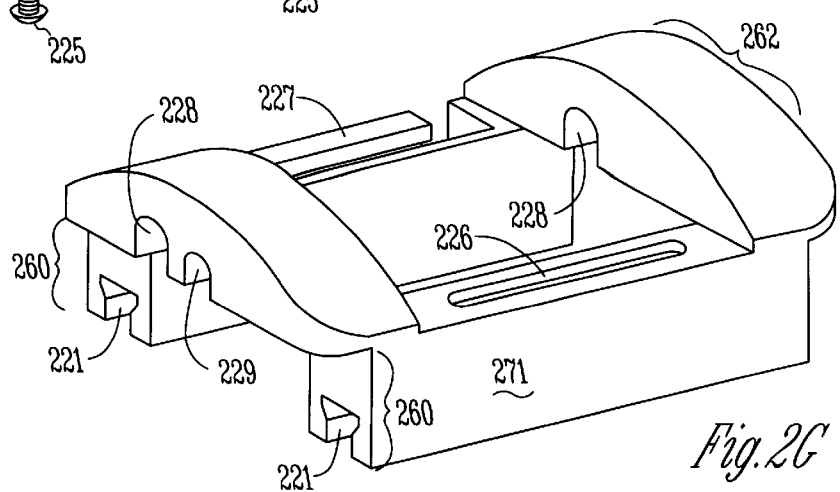
Fig.2F
Fig.2G

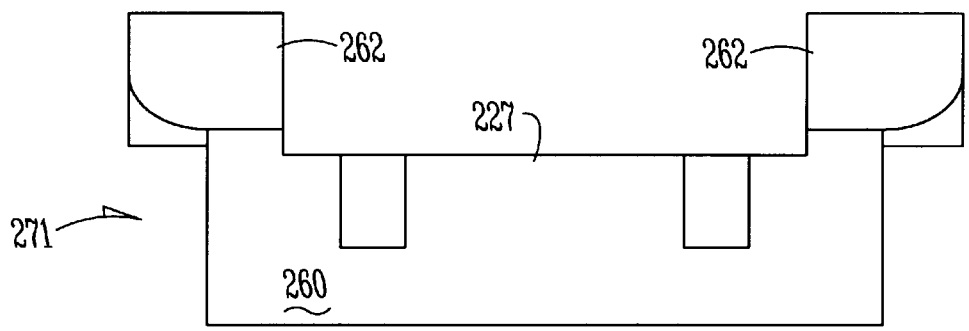
Fig.2H₁
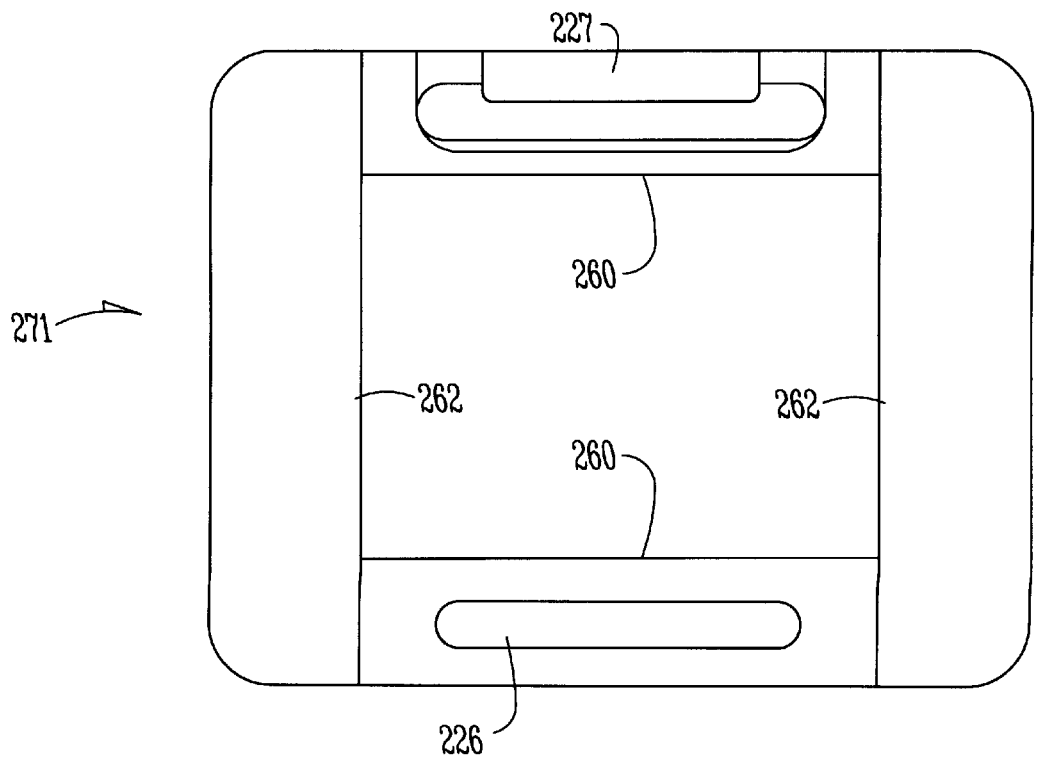
Fig.2H₂

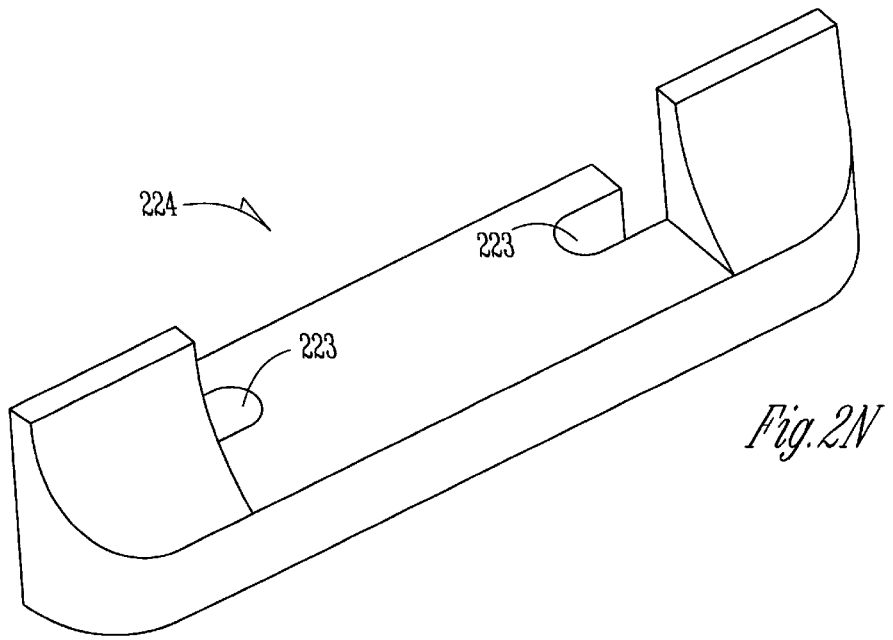
Fig. 2N
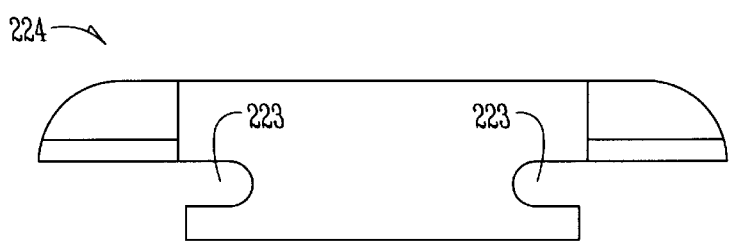
Fig. 2O
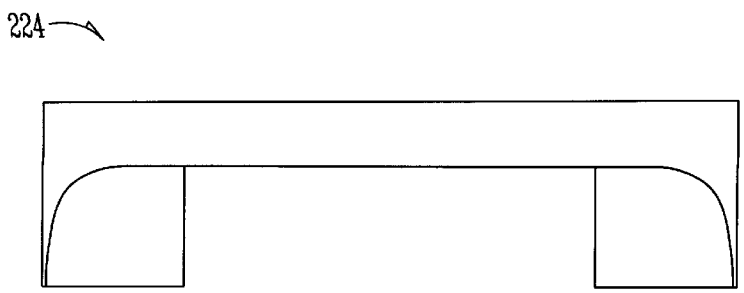 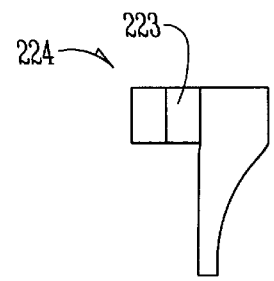
Fig. 2P  Fig. 2Q

APPARATUS FOR HOLDING AND POSITIONING AN ARTERIAL PULSE PRESSURE SENSOR

CROSS-REFERENCES TO RELATED INVENTIONS

This invention is related to co-pending application Ser. No. 08/045,018, filed Mar. 20, 1998, entitled "SENSOR AND METHOD FOR SENSING ARTERIAL PULSE PRESSURE" now allowed and to co-pending application entitled "APPARATUS AND METHOD FOR BLOOD PRESSURE PULSE WAVEFORM CONTOUR ANALYSIS" both filed on even date herewith and incorporated herein by reference.

FIELD OF THE INVENTION

This invention relates to the field of mechanical positioners, and more specifically to a method and apparatus of holding and positioning an arterial pulse pressure sensor relative to the radial artery of a human wrist.

BACKGROUND OF THE INVENTION

Conventionally, blood pressure has been measured by one of four basic methods: invasive, oscillometric, auscultatory and tonometric. The invasive method, also known as an arterial-line method (or "A-line"), typically involves insertion of a needle or catheter into an artery. A transducer connected by a fluid column to the needle or catheter is used to determine exact arterial pressure. With proper instrumentation, systolic, diastolic, and mean arterial pressures may be determined, and a blood-pressure waveform may be recorded. This invasive method is difficult to set up, is expensive and time consuming, and involves a potential medical risk to the patient. Set up of the arterial-line method poses technical problems. Resonance often occurs and causes significant errors. Also, if a blood clot forms on the end of the needle or catheter, or the end of the needle or catheter is located against an arterial wall, a large error may result. To eliminate or reduce these errors, the setup must be checked, flushed, and adjusted frequently. A skilled medical practitioner is required to insert a needle or catheter into the artery, which contributes to the expense of this method. Medical complications are also possible, such as infection, nerve and/or blood vessel damage.

The other three traditional methods of measuring blood pressure are non-invasive. The oscillometric method measures the amplitude of blood-pressure oscillations in an inflated cuff. Typically, the cuff is placed around the upper arm of the patient and then pressurized to different levels. Mean pressure is determined by sweeping the cuff pressure and determining the cuff pressure at the instant the peak amplitude occurs. Systolic and diastolic pressure is determined by cuff pressure when the pressure oscillation is at some predetermined ratio of peak amplitude.

The auscultatory method also involves inflation of a cuff placed around the upper arm of the patient. After inflation of the cuff to a point where circulation is stopped, the cuff is permitted to deflate. Systolic pressure is indicated when Korotkoff sounds begin to occur as the cuff is deflated. Diastolic pressure is indicated when the Korotkoff sounds become muffled or disappear.

The fourth method used to determine arterial blood pressure has been tonometry. The tonometric method typically involves a transducer positioned over a superficial artery. The transducer may include an array of pressure-sensitive elements. A hold-down force is applied to the transducer in order to partially flatten the wall of the underlying artery without occluding the artery. Each of the pressure-sensitive elements in the array typically has at least one dimension smaller than the lumen of the underlying artery in which blood pressure is measured. The transducer is positioned such that at least one of the individual pressure sensitive elements is over at least a portion of the underlying artery. The output from one or more of the pressure sensitive elements is selected for monitoring blood pressure. These tonometric systems either use an upper-arm cuff to calibrate blood-pressure values, or they measure a reference pressure directly from the wrist and correlate this with arterial pressure. However, when a patient moves, recalibration of the tonometric system is often required because the system may experience a change in electrical gains. Because the accuracy of such tonometric systems depends upon the accurate positioning of the individual pressure sensitive element over the underlying artery, placement of the transducer is critical. Consequently, placement of the transducer with these tonometric systems is time-consuming and prone to error. Also, expensive electro-mechanical systems guided by software/hardware computer approaches are often used to assist in maintaining transducer placement.

The oscillometric, auscultatory and tonometric methods measure and detect blood pressure by sensing force or displacement caused by blood-pressure pulses within the underlying artery that is at least partially compressed or flattened. The blood pressure is sensed by measuring forces exerted by blood-pressure pulses in a direction perpendicular to the underlying artery. However, with these methods, the blood-pressure pulse also exerts forces parallel to the underlying artery as the blood-pressure pulses cross the edges of the sensor which is pressed against the skin overlying the underlying artery of the patient. In particular, with the oscillometric and the auscultatory methods, parallel forces are exerted on the edges or sides of the cuff. With the tonometric method, parallel forces are exerted on the edges of the transducer. These parallel forces exerted upon the sensor by the blood-pressure pulses create a pressure gradient across the pressure sensitive elements. This uneven pressure gradient creates at least two different pressures, one pressure at the edge of the pressure sensitive element and a second pressure directly beneath the pressure sensitive element. As a result, the oscillometric, auscultatory and tonometric methods can produce inaccurate and inconsistent blood-pressure measurements.

Further, the oscillometric and auscultatory methods are directed at determining the systolic, diastolic, and/or mean blood-pressure values, but are not suited to providing a calibrated waveform of the arterial pulse pressure.

There is a need to non-invasively obtain an accurate, repeatable blood-pressure waveform from the radial artery.

SUMMARY OF THE INVENTION

The present invention provides a method and a sensor holding and positioning device. In one embodiment, the device includes a sensor base having two feet, the base forming a raised bridge between the two feet. The bridge has one or more cross members spanning all or part of the space between the two feet. A sensor suspension including a sensor holder and sensor-height-adjustment mechanism is coupled by a pivot-arm axle to the sensor base, such that the sensor suspension is able to rotate in an arc about the long axis of the axle. In one such embodiment, the device further includes a pressure sensor attached to the sensor holder of the sensor suspension. In another such embodiment the sensor suspension is able to slide back and forth along a line parallel to the long axis of the axle.

In one embodiment, the two feet are each elongate and they are substantially parallel to one another. In one such embodiment, the axle is also coupled to and between the sensor suspension and the sensor base such that the sensor suspension is able to slide back and forth along a line that is parallel to the long axis of the axle and parallel to the two feet. In another such embodiment, the axle is rotatably coupled to the sensor base such that the long axis of the axle can be rotated about a point on the long axis and thus positioned to each of two or more angular positions.

Another aspect of the present invention provides a sensor holding and positioning device that includes a sensor base having two parallel elongate feet, the base forming a bridge between the two feet with the bridge having two cross members spanning all or part of the space between the two feet, each cross member including a through hole that is parallel to the elongate axes of the feet; and a pivot-arm apparatus. The pivot-arm apparatus includes a sensor suspension including a sensor holding member and an axle extending from two opposite sides of the holding member, the axle mounted in the through holes of the cross members to slide and rotate freely in the through holes, whereby the sensor holder may be slid back and forth between the cross members in a line parallel to the elongate feet and rotated about the axis of the axle.

Yet another aspect of the present invention provides a sensor holding and positioning device that includes a sensor bridge apparatus including one or more feet members on each of opposite sides of a bottom of the apparatus and a pair of cross members on opposite ends of the bridge apparatus and elevated above the feet members, the cross members spanning all or part of the space between the opposite sides of the apparatus, a sensor suspension mounted to the cross members, and a sensor holder held by the sensor suspension in a position between the feet of the sensor bridge apparatus. This allows the sensor holder to be positioned above a desired location on a human or animal body.

Still another aspect of the present invention provides a sensor holding and positioning device that includes a sensor bridge base including one or more feet members and one or more support members elevated above the feet members, a sensor suspension mounted to the support members, and a sensor holder held by the sensor suspension in a position beside one or more feet of the sensor bridge base. This allows the sensor holder to be positioned above a desired location on a human or animal body.

In one such embodiment, this device further includes a pressure sensor attached to the sensor holder of the sensor suspension. In another such embodiment, the device further includes an axle having a long axis, the axle coupled to and between the sensor suspension and the sensor bridge base such that the sensor suspension is able to slide back and forth along a line parallel to the long axis of the axle. In one such embodiment, the axle is also coupled to and between the sensor suspension and the sensor base such that the sensor suspension is able to rotate in an arc about the long axis of the axle.

In another such embodiment, the device further includes a pivot-arm axle having a long axis, the axle coupled to and between the sensor suspension and the sensor base such that the sensor suspension is able to rotate in an arc about the long axis of the axle.

In one such embodiment, the one or more feet members include two feet that are each elongate and substantially parallel to one another. In one such embodiment, the device further includes an axle having a long axis, wherein the axle is coupled to and between the sensor suspension and the sensor base such that the sensor suspension is able to slide back and forth along a line that is parallel to the long axis of the axle and parallel to the two feet.

In one such embodiment, the device further includes an axle having a long axis, the axle is coupled to and between the sensor suspension and the sensor base, wherein the axle is rotatably coupled to the sensor base such that the long axis of the axle can be rotated about a point on the long axis and thus positioned to each of two or more angular positions.

Yet another aspect of the present invention is a method for positioning an arterial pulse-pressure sensor over the radial artery. The method includes the steps of: immobilizing the wrist with a wrist stabilizer; providing a sensor holding and positioning device which includes two or more feet allowing the device to be positioned with at least one of the two or more feet on each of opposite sides of the radial artery and a sensor held by the device between the feet; positioning the device with the sensor above the radial artery and at least one of the two or more feet on each side of the radial artery; and applying the sensor against the human patient's skin overlying the radial artery and urging or pressing the sensor against the radial artery. In one embodiment, the method further includes the step of using a sensor-positioning member included with the device to position an arterial pulse-pressure sensor on top of the radial artery.

Another aspect of the present invention is a pulse-waveform acquisition system. In one embodiment, the system includes a wrist stabilizer, the stabilizer comprising a first member shaped on a forearm portion to conform to contours of a forearm, shaped on a wrist portion to contours of a wrist, and shaped on a proximal hand portion end (an end opposite the forearm portion) to the contours of a hand, and forming an angle of approximately 150 degrees between the forearm portion and the hand portion, the stabilizer further including straps for holding the forearm and hand to the stabilizer. In another embodiment, the system also includes a sensor holding and positioning device, the device comprising: a sensor bridge base including one or more feet members and one or more support members elevated above the feet members; a sensor suspension mounted to the support members; and a sensor holder held by the sensor suspension in a position beside one or more feet of the sensor bridge base. In another embodiment, the pulse-waveform acquisition system further includes a pressure sensor attached to the sensor holder of the sensor suspension.

BRIEF DESCRIPTION OF THE DRAWINGS

FIG. 2D shows an isometric view of one embodiment of sensor holding and positioning device 200.

FIG. 2E shows an exploded isometric view of one embodiment of sensor holding and positioning device 200.

FIG. 2F shows another exploded isometric view of one embodiment of sensor holding and positioning device 200.

FIG. 2G shows an isometric view of one embodiment of sensor-holder base 220 without its rubber feet.

FIG. 2H1 shows a front view of one embodiment of sensor-holder base 220.

FIG. 2H2 shows a top view of one embodiment of sensor-holder base 220.

FIG. 2N shows an isometric view of one embodiment of sensor-base endcap 224.

FIG. 2O shows a bottom view of one embodiment of sensor-base endcap 224.

FIG. 2P shows an end view of one embodiment of sensor-base endcap 224.

FIG. 2Q shows a front view of one embodiment of sensor-base endcap 224.

DESCRIPTION OF PREFERRED EMBODIMENTS

In the following detailed description of the preferred embodiments, reference is made to the accompanying drawings that form a part hereof, and in which are shown by way of illustration, specific embodiments in which the invention may be practiced. It is understood that other embodiments may be utilized and structural changes may be made without departing from the scope of the present invention.

The present invention provides a method and apparatus for stabilizing a person's wrist and for holding and positioning a sensor that non-invasively detects a blood-pressure waveform.

Figure 1A:
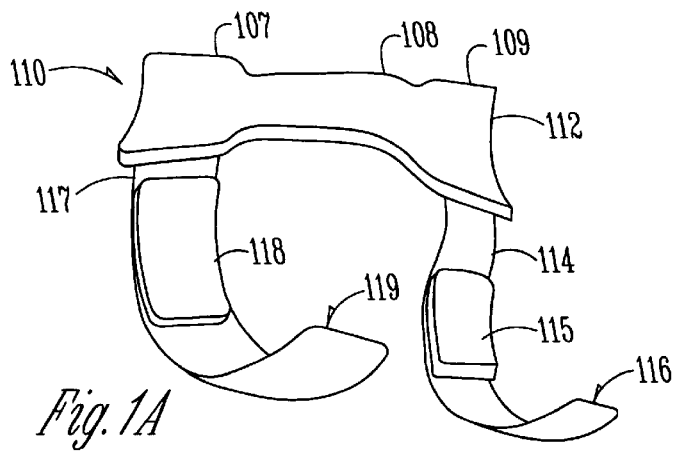
FIG. 1A shows one embodiment of wrist stabilizer 110 of the present invention.

FIG. 1A shows one embodiment of wrist stabilizer 110 of the present invention. Wrist stabilizer base-plate member 112 has a forearm portion 107 that, in this embodiment, is shaped to conform to the contours of a patient's forearm (the term "patient" denotes broadly the person whose blood pressure is being sensed, and could be either a patient being treated medically, or a human subject in a clinical research trial, or any other person or animal whose blood pressure is to be sensed), a wrist portion 108 that is shaped to conform to the contours of a wrist, and a hand portion that is shaped to conform to the contours of a hand, and forming a forearm-hand angle of approximately 150 degrees between the forearm portion 107 and the hand portion 109, the stabilizer 110 further including straps 114 and 117 (for example, made from hook-and-loop material fabric wherein loop material is used for the straps, and hook material is fastened to base-plate member 112) for holding the patient's forearm and hand to the stabilizer 110. In one embodiment, forearm strap 117 optionally includes a pad 118 to pad the patient's forearm, and a hook-and-loop fastener 119 (such as Velcro®-brand fastener material or other similar medical-equipment-grade fastener material) to removeably fasten the strap; and hand strap 114 includes a hand pad 115 to pad the patient's palm next to the fingers and the proximal portion of the fingers, and a hook-and-loop fastener 116 (such as Velcro®-brand fasteners) to removeably fasten the strap around the hand and back to the stabilizer base member 112. Base-plate member 112 is rigid, and preferably made of light-weight metal alloy or sturdy plastic material. In one embodiment, for the subject's comfort, base plate 112 is covered with a closed-cell foam pad (such as Neoprene-brand foam rubber), covered with a skin-compatible fabric.

In one embodiment, the length of the hand portion 109 of the wrist stabilizer is made long enough, and the attachment position of hand strap 114 to hand portion 109 of the wrist stabilizer are such that hand strap 114 is placed over at least the proximal end of the fingers of patient 99, in order that patient 99 is not tempted or encouraged to clench their hand into a fist. The fingers of patient 99 are thus encouraged to be in a relaxed, semi-open position for better blood-pressure waveform acquisition and measurement.

Figure 1B:
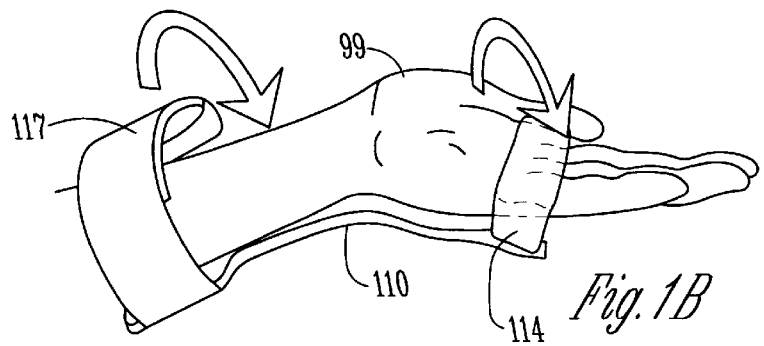
FIG. 1B shows one embodiment of wrist stabilizer 110 being applied to the left hand of a human patient 99.
Figure 1C:
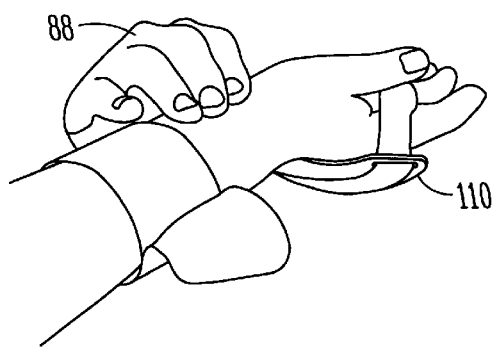
FIG. 1C shows a healthcare professional 88 determining one optimal location to apply the sensor of the present invention.
Figure 1D:
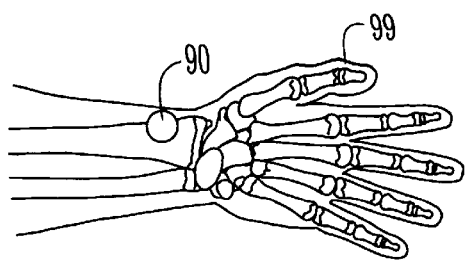
FIG. 1D shows one optimal location for sensing a blood-pressure waveform from the radial artery of the left hand of a human patient 99.

FIG. 1B shows one embodiment of wrist stabilizer 110 being applied to the left hand of a patient 99 using straps 114 and 117. (Some of the drawings herein show the left hand being used, and others show the right hand being used. The present invention can be used on either hand, adjusting for the complementary symmetry of the body.) FIG. 1C shows a healthcare professional 88 palpating the wrist to determine an optimal location overlying the radial artery to which to apply the sensor of the present invention. FIG. 1D shows a schematic of the anatomy of the left human hand, showing an optimal location for sensing a blood-pressure waveform from the radial artery.

One purpose of wrist stabilizer 110 is to extend the hand slightly back in order to stabilize or immobilize the wrist joint, and to stabilize the radial artery and bring it near the skin in order to obtain a good blood-pressure waveform. This provides the advantages of giving greater patient comfort and obtaining a better waveform. Another purpose of wrist stabilizer 110 is to hold the hand and fingers of patient 99 in a relaxed, semi-extended or open position (as opposed to a closed or clenched-fist position). This provides the advantage that each measurement is made from a relaxed and repeatable position, consistent blood flow is achieved, and a good blood-pressure waveform may be obtained. Yet another purpose of wrist stabilizer 110 is to provide a spacer relative to strap 250 in order to distribute the force from strap 250 over a larger area and to provide one or more spaces between strap 250 and the sides of the wrist, so that adequate venous return blood flow is achieved. This provides the advantages of providing greater patient comfort, reduced red marks from strap pressure on the skin of patient 99, and minimization of edema and swelling of the hand of patient 99. Wrist stabilizer 110 should leave the area overlying the radial artery that is to be sensed as open and unobstructed as possible (in order that the healthcare professional 88 can readily palpate the artery, and then apply the sensor to the proper location), while immobilizing the wrist and radial artery (in order that a successive series of waveforms can be obtained under conditions that are consistent, repeatable and reproducible).

Figure 1E:
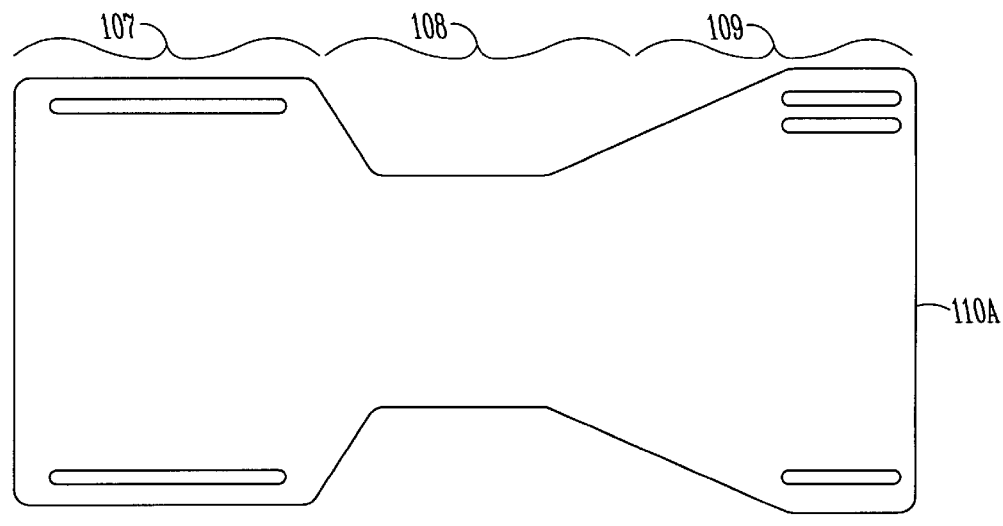
FIG. 1E shows a top view, before shaping, of another embodiment of wrist stabilizer 110.
Figure 1F:
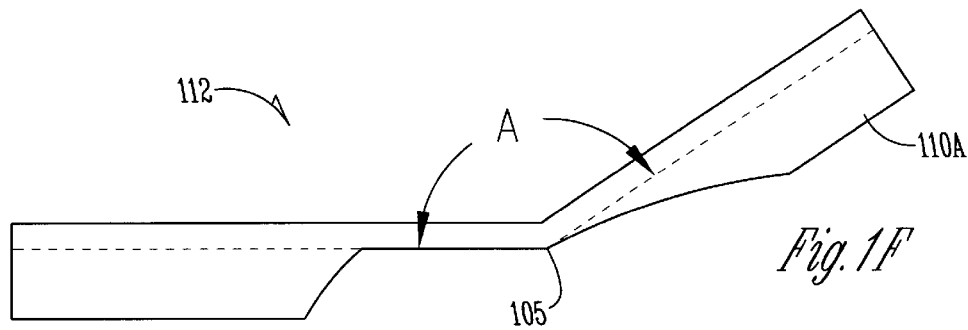
FIG. 1F shows a side view, after shaping, of the FIG. 1E embodiment of wrist stabilizer 110.
Figure 1G:
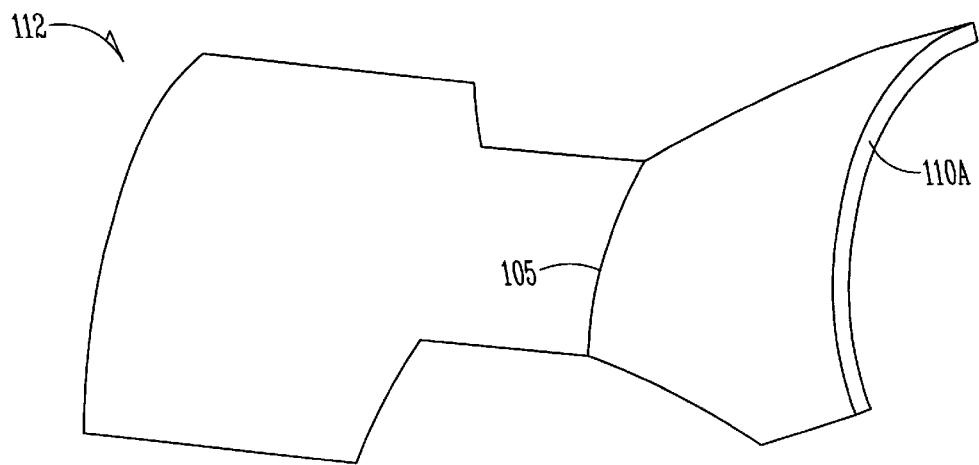
FIG. 1G shows an isometric view, after shaping, of the FIG. 1E embodiment of wrist stabilizer 110.

FIG. 1E shows a top view, before shaping, of the rigid plastic blank 110A for another embodiment of wrist stabilizer base plate 112. FIG. 1F shows a side view, after shaping, of the FIG. 1E embodiment of wrist stabilizer base plate 112. FIG. 1G shows an isometric view, after shaping, of the FIG. 1E embodiment of wrist stabilizer base 112. In one embodiment, wrist stabilizer base 112 includes a closed-cell neoprene rubber cushion having a skin-compatible nylon taffeta cloth covering on its skin-contact surface. In applying wrist stabilizer 110, the bend 105 is placed at the skin crease that forms on the back of the wrist when the patient's wrist is bent slightly backwards, strap 117 is attached first, and then strap 114 is attached.

Figure 2A:
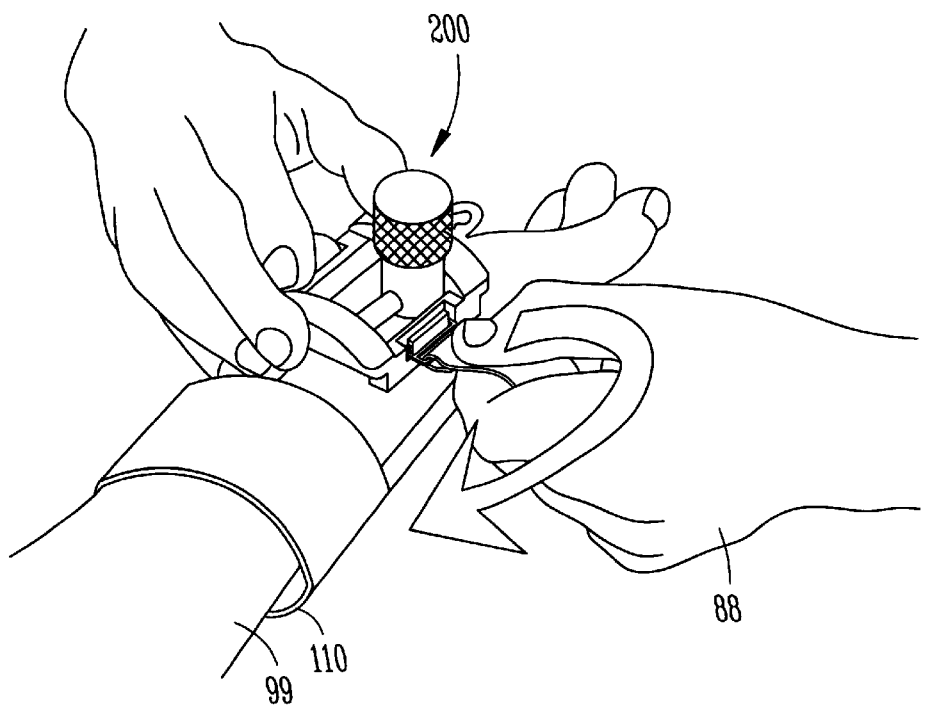
FIG. 2A shows a healthcare professional 88 applying a sensor holding and positioning device 200 of the present invention.
Figure 2B:
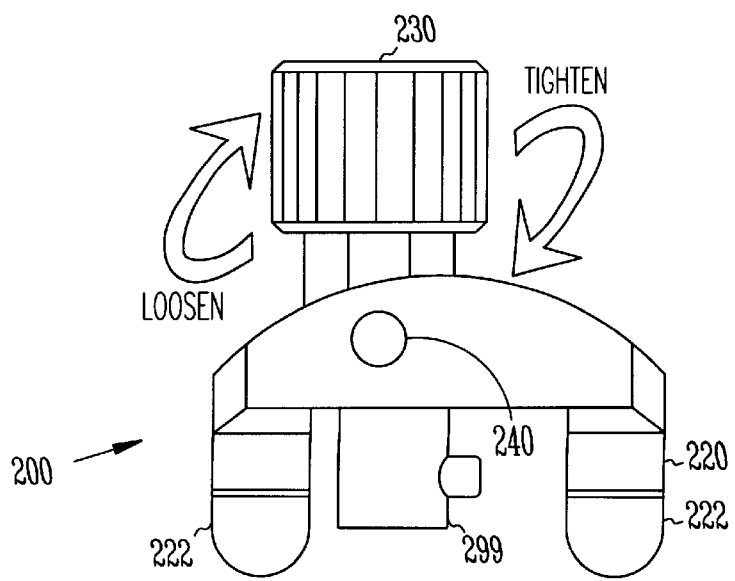
FIG. 2B shows an end view of one embodiment of sensor holding and positioning device 200 of the present invention, with an attached sensor 299.

FIG. 2A shows a healthcare professional 88 applying a sensor holding and positioning device 200 of the present invention to the right wrist of a human subject 99. In the embodiment shown, axle 240 is closer to one (foot 222.1) of the two elongated rubber feet 222 (leaving a larger opening or window between the axle 240 and the other foot 222.2), and it is this rubber foot 222.1 that is placed at the radial aspect (by the thumb side) of the wrist, and the other foot 222.2 is placed near the center of the wrist. This places the space or window between the other foot and axle 240 towards the center of the wrist, in order to provide a better view of sensor 299 and its relationship to the location of the radial artery, as previously determined by palpation (or by marking a dot or small X on the skin with a pen at a point estimated by the healthcare professional). The long axes of both feet are aligned to be substantially parallel to the radial artery, one on either side of the artery. FIG. 2B shows an end view of one embodiment of sensor holding and positioning device 200 of the present invention, with an attached sensor 299. When applied to the right arm, this end is preferably closest to the patient's hand, while when applied to the left arm, this end is preferably closest to the patient's elbow, in order that sensor 299 can be more easily positioned directly over the radial artery. By locating axle 240 to one side of the opening between the feet (rather than directly in the center of the opening), a better view is afforded to the sensor 299 when the sensor holding and positioning device 200 is in place on the patient's arm. This arrangement also orients the sensor over the radial artery while still providing a stable placement of both feet of sensor holding and positioning device 200 upon the wrist of patient 99. In embodiments in which the axle is centered, the thumb-side foot tends to slide off the side of the patient's wrist, particularly for small wrists as are found with a 5th percentile female. Sensor suspension 230 includes a height-adjustment mechanism (such as the screw-adjustment shown) in order that the height of the sensor can be adjusted to obtain an optimal amount of hold-down pressure between the sensor 299 and the patient's skin overlying the radial artery (i.e., the proper amount of compression on the artery to obtain a good blood-pressure waveform signal). Sensor-holder base 220 (including rubber feet 222) provides a stable base.

Figure 2C:
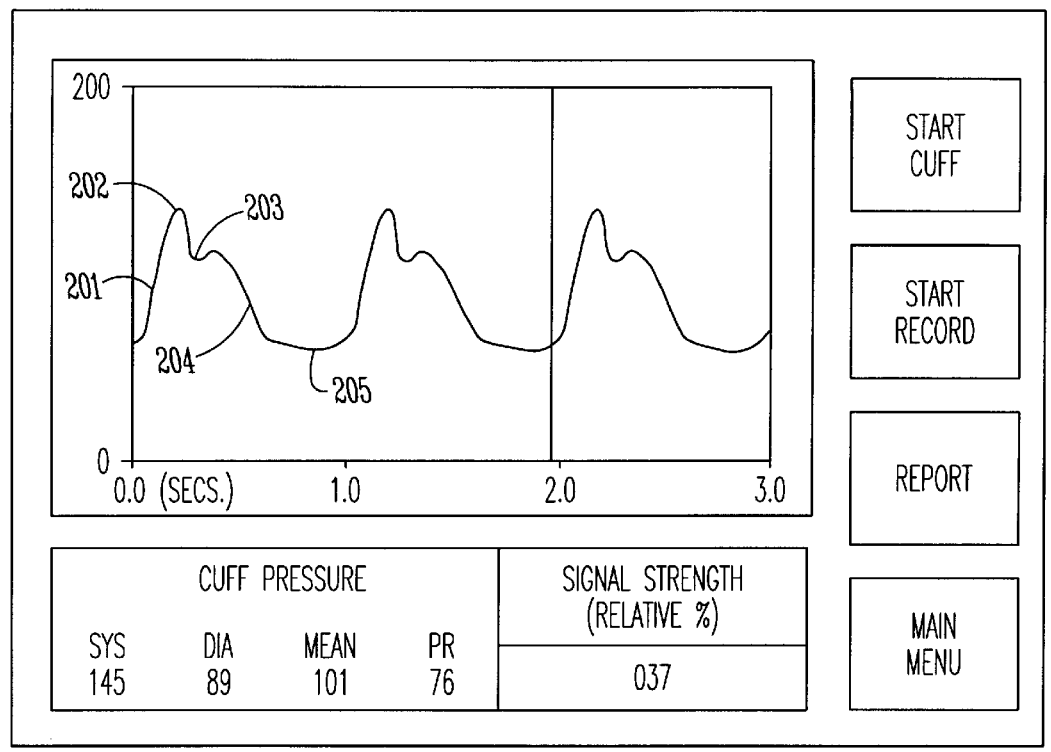
FIG. 2C shows a graph of radial artery pressure versus time showing the dicrotic notch and other features of the blood-pressure waveform.

FIG. 2C shows a graph of a exemplary blood-pressure waveform of radial artery pressure versus time (on a representative screen display) showing the dicrotic notch and other features of the blood-pressure waveform. The graph shows three heart beats, each having a systolic upswing portion 201, a peak systole portion 202, a dicrotic notch portion 203, a diastolic decay curve portion 204, and a trough diastole portion 205. In one embodiment, the hold-down pressure of sensor 299 is adjusted until the dicrotic notch has a "best shape" (i.e., a relatively deep notch) as visually observed by the healthcare professional viewing a screen display such as is shown in FIG. 2C. In one such embodiment, a software analysis of signal strength is performed, and output as a value or visual or audio indication of approximate or relative (e.g., percentage) signal strength. In one embodiment, the hold-down pressure of sensor 299 is adjusted until the best value for relative signal strength is obtained. In one embodiment, an automatic pneumatic arm cuff (as are well known in the art) is used to obtain values (i.e., cuff pressures—traditionally in mm Hg) for systolic (SYS), diastolic (DIA), and arterial mean (MEAN) blood-pressure values, and a pulse rate (PR) value, and these cuff pressures are used to calibrate the blood-pressure waveform obtained by sensor 299 from the radial artery.

FIG. 2D shows an isometric view of one embodiment of sensor holding and positioning device 200. Sensor holding and positioning device 200 includes sensor-holder base 220, sensor suspension 230, and axle 240. Strap 250 is used to hold sensor-holder base 220 to the wrist of the patient 99. Axle 240 couples sensor suspension 230 to sensor-holder base 220, allowing sensor suspension 230 to slide back and forth (reference 238) along the long axis 241 of axle 240, and to rotate in an arc (reference 239) about the long axis 241. This allows the sensor suspension 230 to be positioned to the location palpated by the healthcare professional (after the sensor-holder base 220 is strapped to the wrist of patient 99), and then rotated around arc 239 so that the bottom surface of sensor 299 is generally parallel to the skin surface (and thus this plane is parallel to the long axis of the underlying radial artery). Sensor base feet 260 raise the rest of sensor-holder base 220 off of the wrist of patient 99, so that the radial artery is not compressed or obstructed by sensor-holder base 220. Sensor base cross members 262 form a bridge spanning the space above and between the two feet 260. In one embodiment, cushions 222 (e.g., in one embodiment, two identical parts are used, each having approximately a "D" shaped cross section, and a 0.250" hole in its center; and are manufactured by an extrusion process; the material, in one embodiment, is Santoprene® 181-64) are provided on the bottom of feet 260 for the patient's comfort and for non-slip and non allergenic positioning on the skin of the patient's wrist.

FIG. 2E shows an exploded isometric view of one embodiment of sensor holding and positioning device 200. FIG. 2F shows another exploded isometric view of one embodiment of sensor holding and positioning device 200. Sensor holding and positioning device 200 includes sensor-holder base 220, sensor suspension 230, and axle 240. Strap 250 is used to hold sensor-holder base 220 to the wrist of the patient 99. In one embodiment, the ends of axle 240 are slidably and rotatably fitted into slots 228, and held in place by base endcaps 224. One end of strap 250 is held in slot 226 by pin 252. The other end of strap 250 has a plastic loop 256 which retains plastic buckle 254 which fits over post 227 on base unit 271.

Figure 2I:
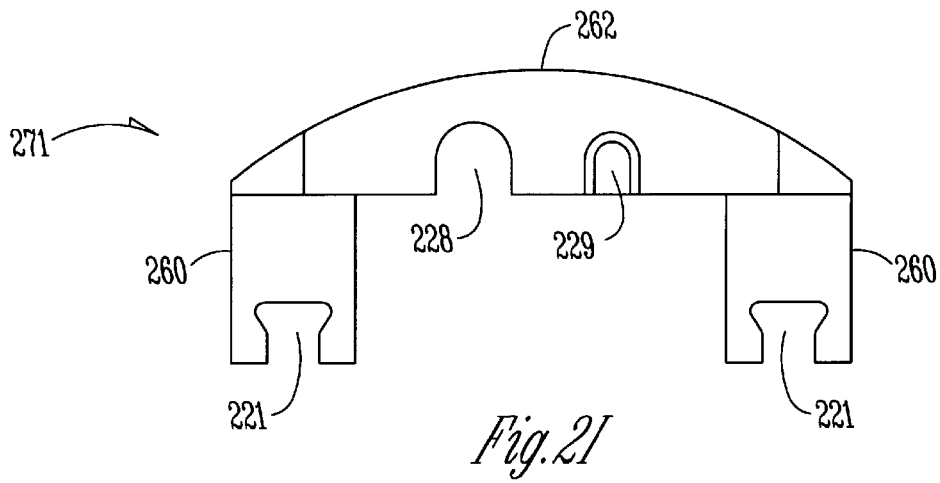
FIG. 2I shows an end view of one embodiment of sensor-holder base 220.
Figure 2J:
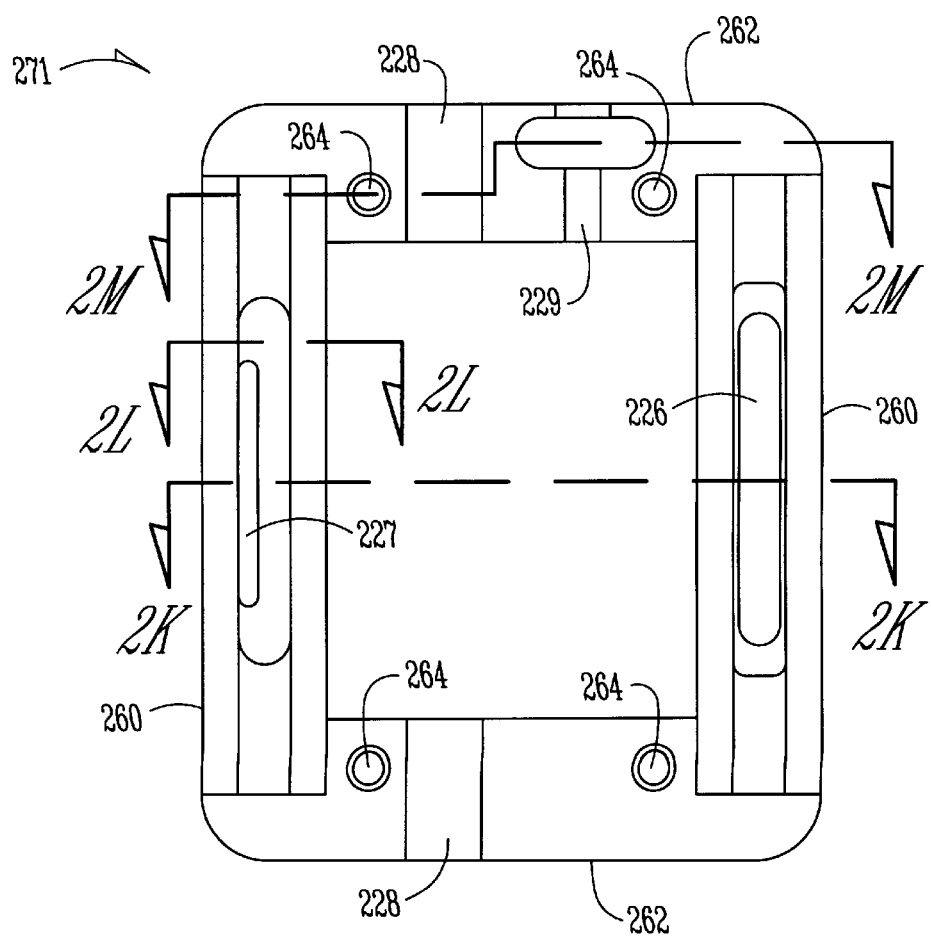
FIG. 2J shows a bottom view of one embodiment of sensor-holder base 220.
Figure 2K:
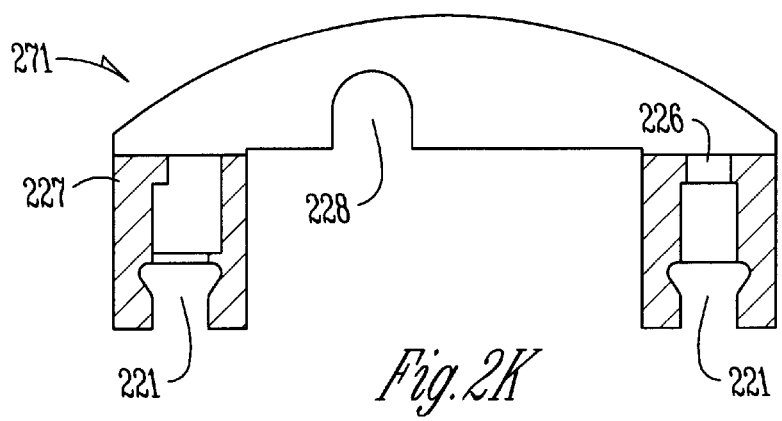
FIG. 2K shows a section A—A of one embodiment of sensor-holder base 220.
Figure 2L:
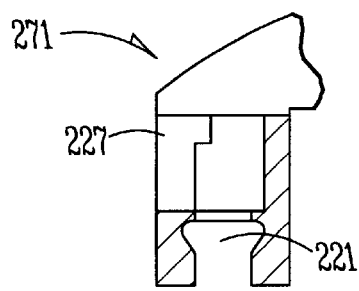
FIG. 2L shows a section B—B of one embodiment of sensor-holder base 220.
Figure 2M:
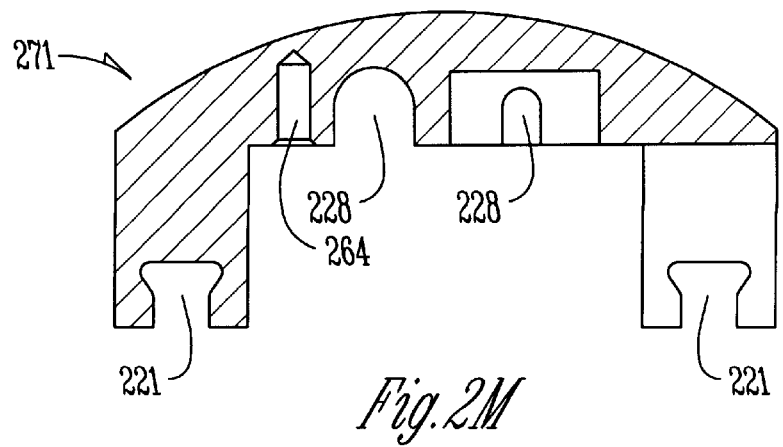
FIG. 2M shows a section C—C of one embodiment of sensor-holder base 220.
Figure 2R:
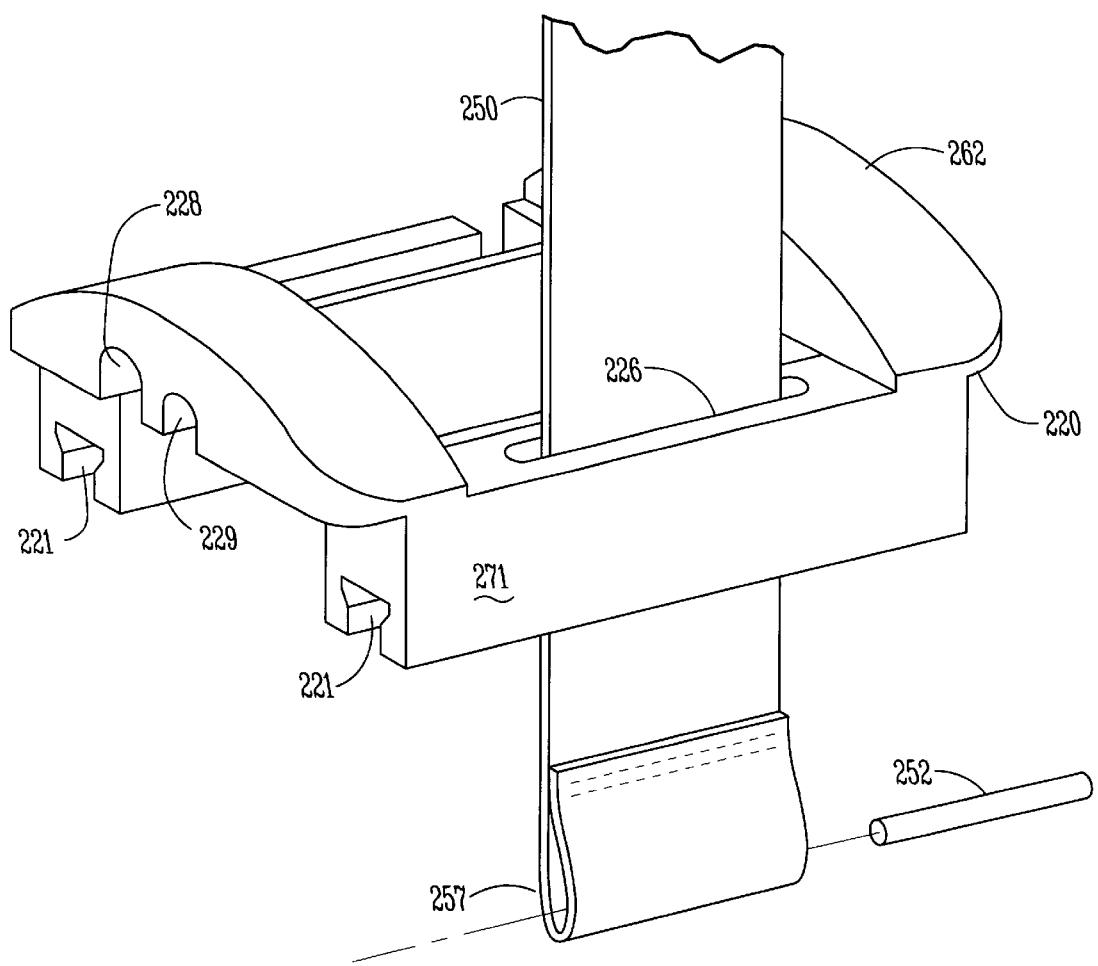
FIG. 2R shows an isometric view of the attachment method for one embodiment of strap 250.

Note that in the embodiment shown in FIGS. 2A, 2D, 2E, 2G, 2J, and 2K, post 227 is in the foot 260 that is closest to axle 240. Another embodiment that is preferred is shown in FIGS. 2F and 2R, in which post 227 is in the foot 260 that is furthest from axle 240, and adjacent to observation window 261.

Strap 250 slides through buckle 254 and attaches to itself using hook-and-loop fastener material 255, in order to adjust the length of the strap 250 once strap 250 is fastened around the wrist of patient 99 fitted with a wrist stabilizer. Cushions 222 are inserted into dovetail slots 221, and are also held in place by endcaps 224. Endcaps 224 are held in place by bolts 225 which go into tapped holes in base unit 271. In the embodiment shown, the two ends of axle 240 are permanently affixed to either side of sensor suspension 230 such that both of their axes align with one another (externally, they appear as a single axle, however, internal to sensor suspension, the screw height adjustor 233 passes between them). Sensor suspension 230 includes suspension base 231, knob 232, screw height adjustor 233, and screw 234. Screw 234 is used to attach to sensor 299 which has a cable 291, wherein the cable 291 is held in place in slot 229 by an endcap 224. In one embodiment, all parts of sensor holding and positioning device 200 except for strap 250 and cushions 222 are made from medical-grade stainless steel, while in another embodiment, aluminum is used for some or all parts.

FIG. 2G shows an isometric view of one embodiment of sensor-holding-and-positioning-device base unit 271 without its rubber feet 222. FIG. 2H1 shows a front view, FIG. 2H2 shows a top view, FIG. 2I shows an end view, FIG. 2J shows a bottom view, FIG. 2K shows a section A—A, FIG. 2L shows a section B—B, and FIG. 2M shows a section C—C; all are views of the sensor-holding-and-positioning-device base unit 271 of FIG. 2G. Cushions 222 (see FIG. 2F) are inserted into dovetail slots 221, and form part of the two feet 260 of the sensor holding and positioning device 200. Slot 226 and post 227 are used to attach to strap 250 (see FIG. 2F). Slots 228, once endcaps 224 are fixed in place (see FIG. 2F), form through-holes that hold the ends of axle 240, in order that axle 240 can be positioned (e.g., slid) back and forth along its long axis, and rotated about its long axis. In the embodiment shown, the sensor base is approximately 2.7 inches by 2.1 inches (i.e., in this embodiment, the outer edges of feet 260 are 2.11 inches apart, and the outer edges of bridge cross members 262 are 2.665 inches apart).

In another embodiment (not shown), axle 240 is non-slidably attached to bridge cross members 262. In one such embodiment, axle 240 is rotatably attached to bridge cross members 262 such that axle 240 and sensor suspension 230 can be rotated in an arc about the long axis of axle 240. In another such embodiment, axle 240 is rotatably attached to sensor suspension 230 such that sensor suspension 230 can be rotated in an arc about the long axis of axle 240. In yet another such embodiment, axle 240 is non-rotatably and non-slidably attached to both sensor-holder base 220 and to sensor suspension 230 in order to be held in a fixed relationship to each. In each of these embodiments, sensor-holder base 220 has one or more feet 260 that are to be positioned along side (i.e., no over) the artery to be sensed. Preferably two feet 260 are used, one on either side of the artery being sensed.

FIG. 2N shows an isometric view of one embodiment of sensor-base endcap 224. FIG. 2O shows a bottom view, FIG. 2P shows an end view, and FIG. 2Q shows a front view, all of the sensor-base endcap 224 of FIG. 2N. Endcap 224 is attached using bolts 225 into drilled and tapped holes 264 of base unit 271. Once in place, endcap 224 holds cushions 222, axle 240, and cable 291 into their respective slots 221, 228, and 229.

FIG. 2R shows an isometric view of the attachment method for one embodiment of sensor-base strap 250. In this embodiment, strap 250 has a loop 257 sewn into one end, pin 252, which is longer than the length of slot 226 and/or wider than the width of slot 226 at its top, is positioned through loop 257, and the strap 250 is raised through slot 226 so that the pin 252 keeps the loop end of strap 250 within slot 226.

Figure 2S:
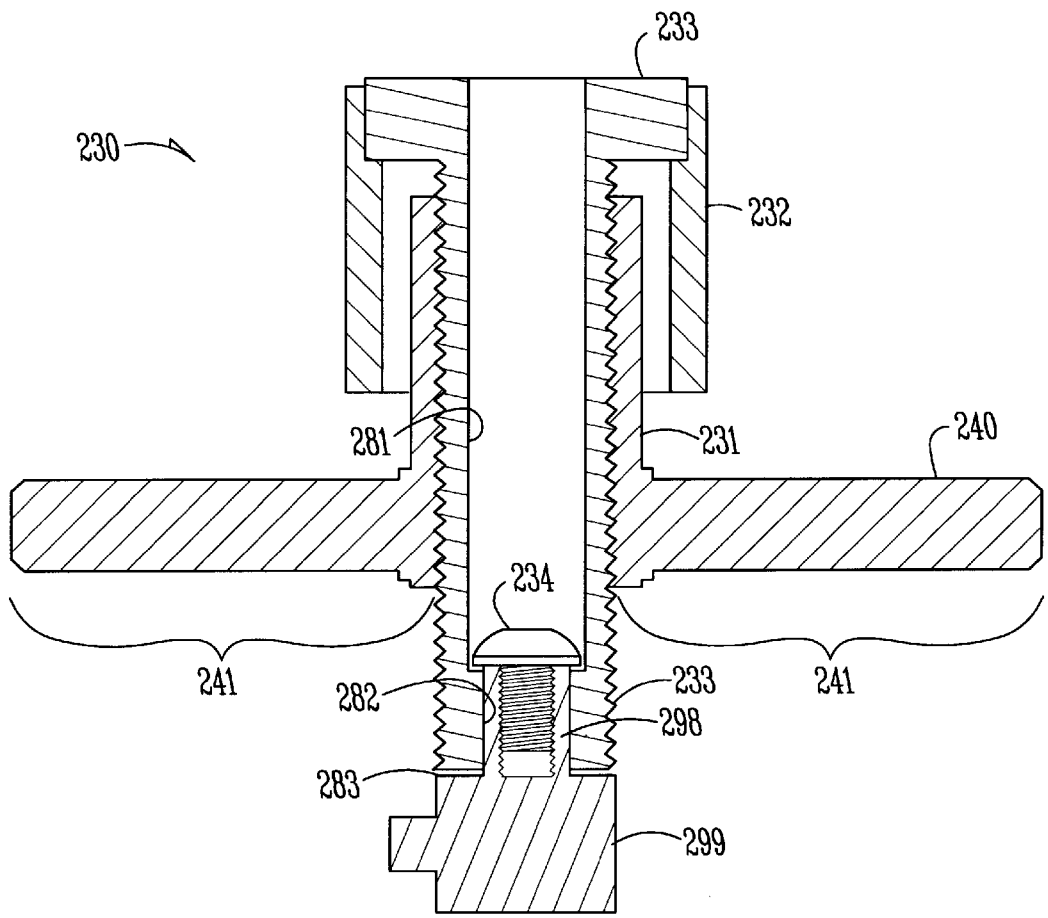
FIG. 2S shows a cross-section view of one embodiment of sensor suspension 230.

FIG. 2S shows a cross-section view of one embodiment of sensor suspension 230. In the embodiment shown, threaded stainless-steel screw 233 is press-fit to knob 232. This assembly is threaded into pivot arm 241. In this embodiment, pivot arm 240 includes housing 231 having female threads, and axles 240, all fabricated as a single piece of metal. Boss 298 on sensor 299 is made longer than the hole in the end of screw 233, in order that a small top clearance 281 and bottom clearance 283 exist, in order to provide a free swiveling connection between suspension 230 and sensor 299. Button-head screw 234 can thus be tightened without binding the sensor 299 to suspension 230.

Figure 3A:
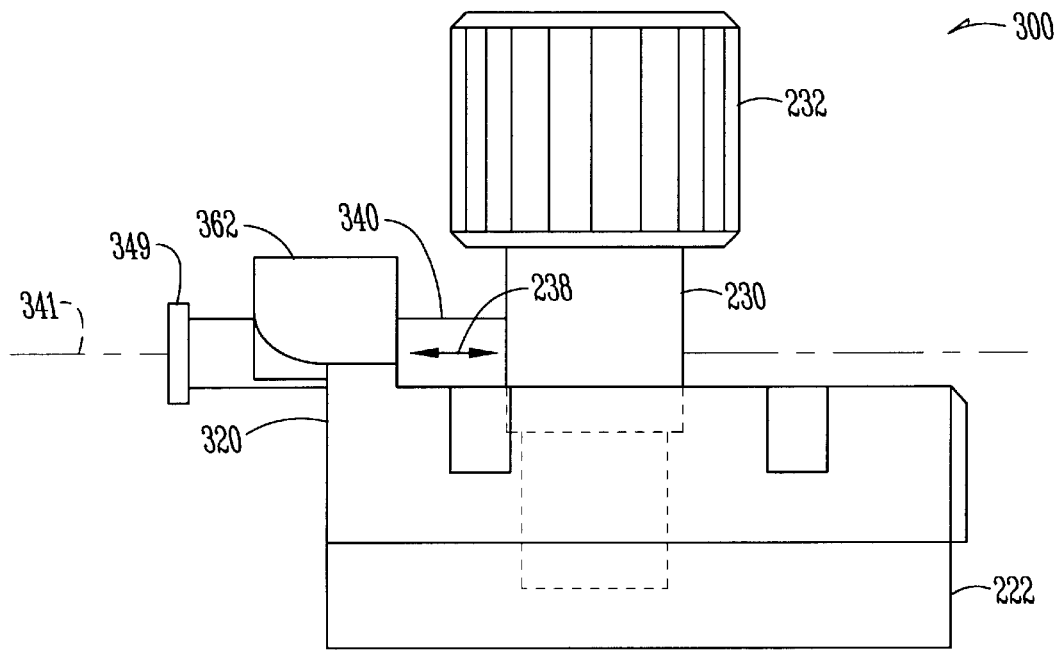
FIG. 3A shows a front view of one embodiment of sensor holding and positioning device 300.
Figure 3B:
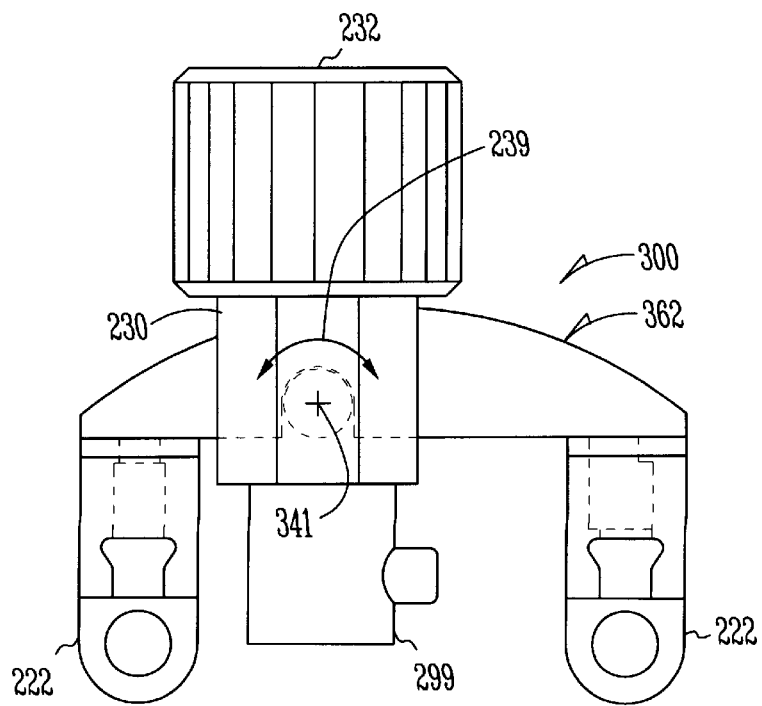
FIG. 3B shows a end view of one embodiment of sensor holding and positioning device 300.
Figure 3C:
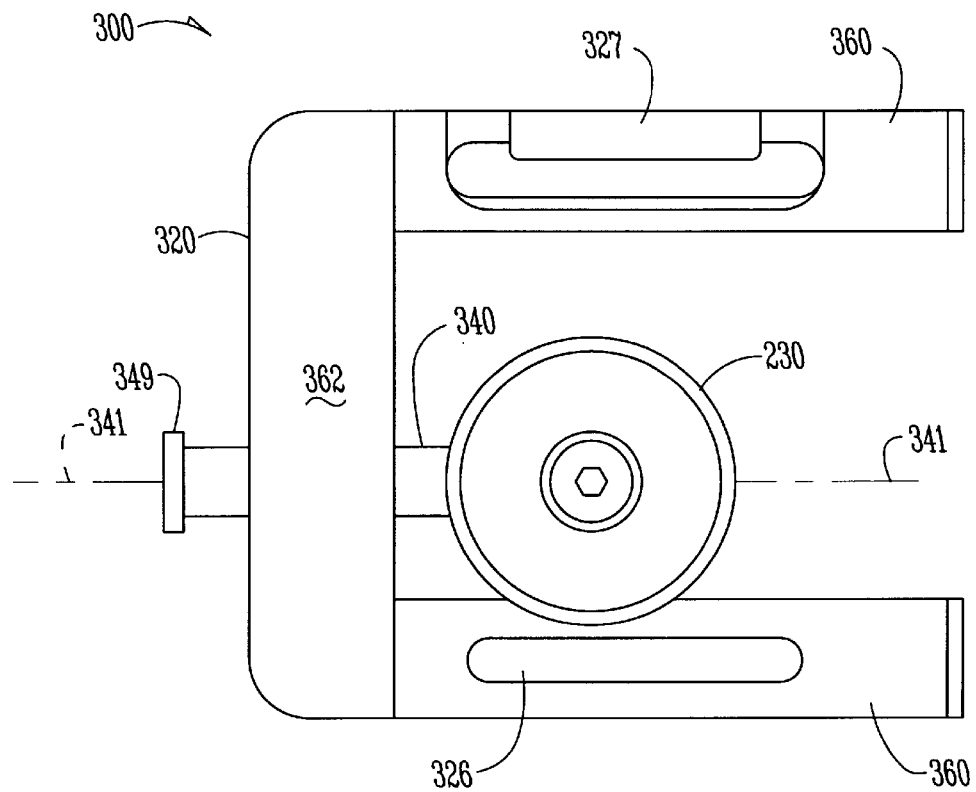
FIG. 3C shows a top view of one embodiment of sensor holding and positioning device 300.
Figure 3D:
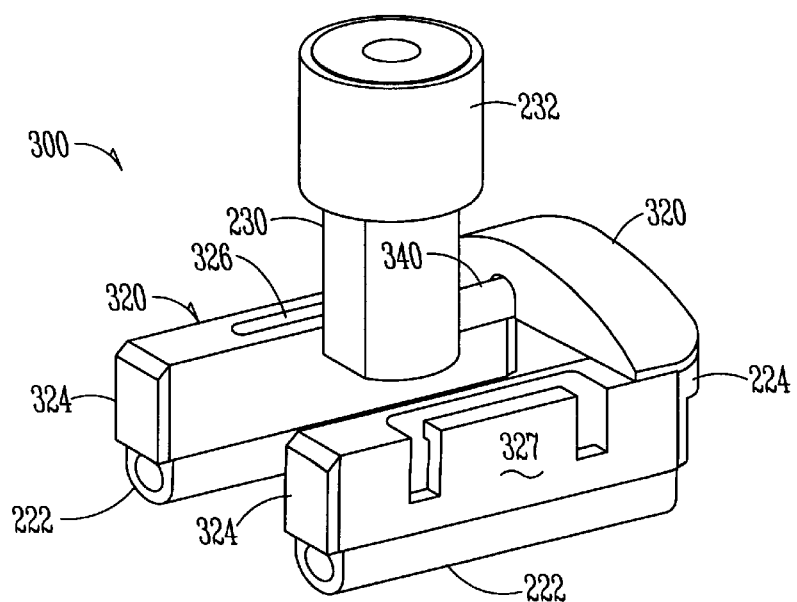
FIG. 3D shows an isometric view of one embodiment of sensor holding and positioning device 300.
Figure 4A:
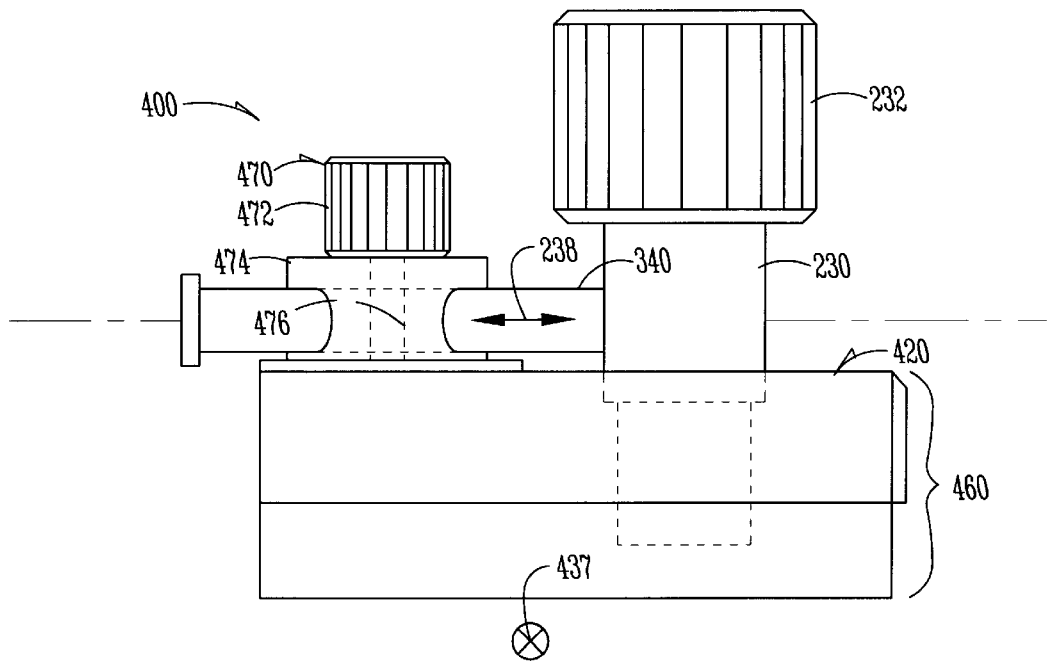
FIG. 4A shows a front view of one embodiment of sensor holding and positioning device 400.
Figure 4B:
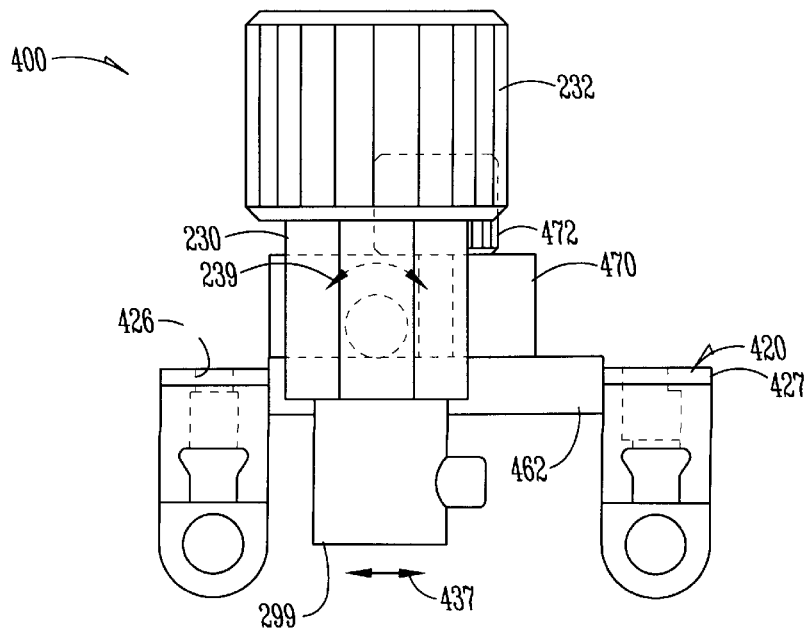
FIG. 4B shows a end view of one embodiment of sensor holding and positioning device 400.
Figure 4C:
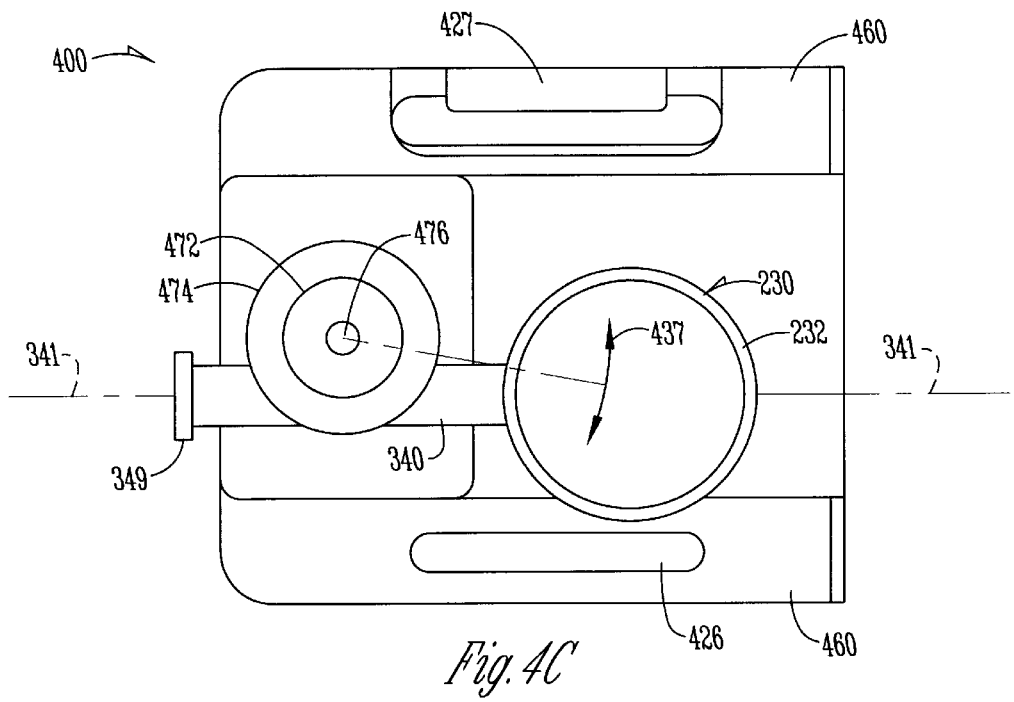
FIG. 4C shows a top view of one embodiment of sensor holding and positioning device 400.

FIG. 3A shows a front view of one embodiment of sensor holding and positioning device 300 (sensor holding and positioning device 300 is one alternative embodiment of sensor holding and positioning device 200 of FIGS. 2A–2R and sensor holding and positioning device 400 of FIGS. 4A–4C). FIG. 3B shows a end view, FIG. 3C shows a top view, and FIG. 3D shows an isometric view, all of this embodiment of sensor holding and positioning device 300. In this embodiment, sensor holding and positioning device 300 provides function and features substantially identical to sensor holding and positioning device 200, except that only one bridge cross member 362 is provided. This allows a better view of sensor 299 as it is applied to the skin surface of patient 99. In the embodiment shown, sensor base 320 has only a single bridge cross member 362 spanning and connecting the two feet 360. Axle 340 has a knob 349 to prevent excess travel of the axle 340 as it is slid back and forth along its long axis 341. Axle 340 can thus be freely moved back and forth (reference 238) along its long axis 341, and sensor suspension 230 can be freely rotated (reference 239) about long axis 341. Endcaps 324 are attached (e.g., by epoxy adhesive or screws) to the ends of feet 360 to hold cushions 222 in place. Slot 326 and post 327 provide the same respective functions as slot 226 and post 227 of sensor holding and positioning device 200 of FIGS. 2A–2R.

FIG. 4A shows a front view of one embodiment of sensor holding and positioning device 400 (sensor holding and positioning device 400 is one alternative embodiment of sensor holding and positioning device 200 of FIGS. 2A–2R and sensor holding and positioning device 300 of FIGS. 3A–3D). FIG. 4B shows a end view of this embodiment of sensor holding and positioning device 400. FIG. 4C shows a top view of this embodiment of sensor holding and positioning device 400. In this embodiment, sensor holding and positioning device 400 provides function and features substantially identical to sensor holding and positioning device 300 of FIGS. 3A–3D, except that axle 340, using rotation mechanism 470, can be rotated (reference 437) in a horizontal plane (parallel to the plane passing through the long axes of feet 460) to two or more angular positions so that the sensor can be moved closer to one or the other of the two feet 460. In the embodiment shown, knob 472 is used to loosen or tighten screw 476 to allow cylinder 474 to freely rotate, or to be locked in position, respectively. In one such embodiment, tightening knob 472 also locks sensor suspension relative to rotating in direction 239, while in another embodiment it does not. In one such embodiment, tightening knob 472 also locks sensor suspension relative to sliding back and forth in direction 238, while in another embodiment it does not. In all other ways, sensor holding and positioning device 400 has the same functions and the same respective parts as sensor holding and positioning device 300.

In another embodiment, (not shown) a rotation mechanism such as rotation mechanism 470 of FIGS. 4A–4C is provided on a corresponding base having two or more cross members (such as cross members 262 on sensor-holder base 220 of FIGS. 2A–2R), wherein an axle 340 is attached only to the rotation mechanism.

In each of the above embodiments, a screw height-adjustment mechanism is provided (e.g., sensor suspension 230, which has a screw adjustment mechanism 233). In other embodiments, other manual adjustment mechanisms are provided, such as a plunger with a set-screw-knob locking mechanism (see FIG. 5), or a ratchet and pawl, or other suitable height-adjustment mechanisms are used.

In one such embodiment, a pneumatic (or hydraulic) syringe is used (see FIG. 9), wherein a computer-based analysis of the signal from sensor 299 is performed, and the hold-down pressure is pneumatically (or hydraulically) adjusted by the computer until a satisfactory signal is obtained.

Figure 5:
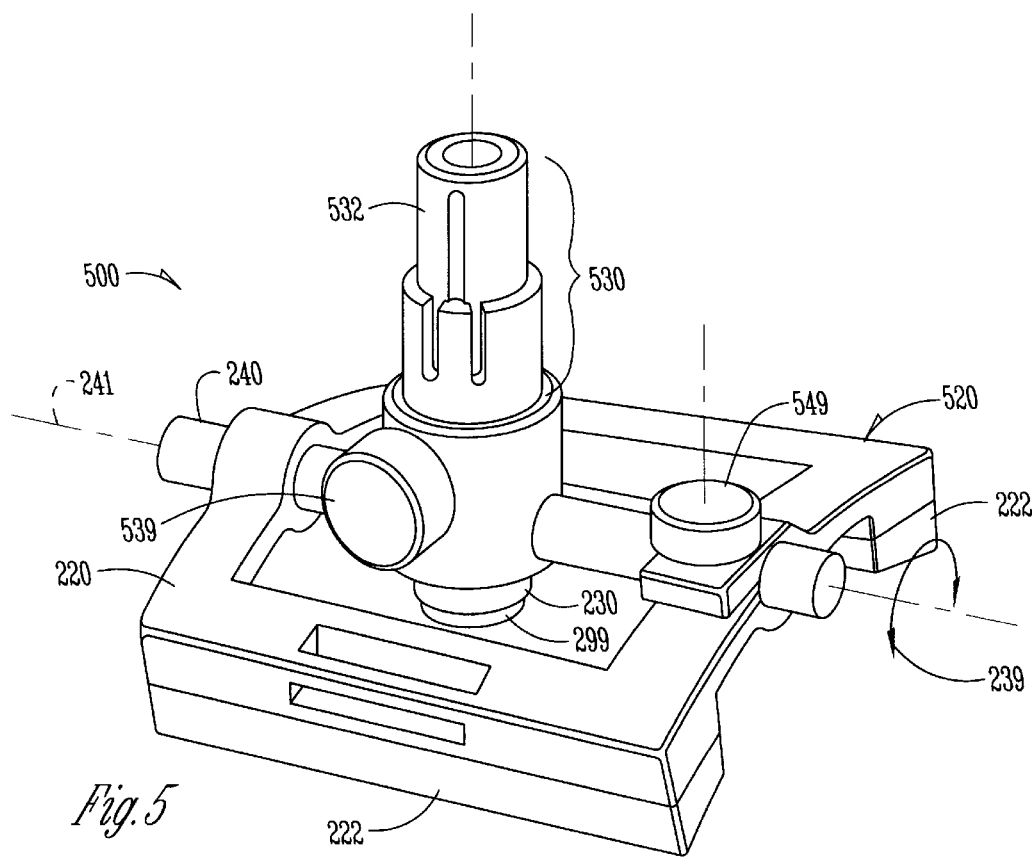
FIG. 5 shows an isometric view of one embodiment of sensor holding and positioning device 500 according to the present invention.

FIG. 5 shows an isometric view of one embodiment of sensor holding and positioning device 500 according to the present invention. Sensor holding and positioning device 500 is functionally similar to sensor holding and positioning device 200, except that a set-screw locking knob 539 is provided for gross height adjustment and knob 532 is provided for fine hold-down-pressure adjustment. Clicker X snaps into groove Y to count the number of revolutions used to attain proper hold-down pressure. This assists the healthcare professional in attaining repeatable results (for example in a second test) by providing a starting point with which to begin subsequent tests. Set-screw locking knob 549 is provided to lock axle 240 in a fixed position once sensor suspension 530 is in position so that sensor 299 is over the desired location overlying the radial artery. In one such embodiment, set-screw locking knob 549 when loose, allows axle 240 to freely slide back and forth along the X-axis 241, and to freely rotate (reference 239) about the X-axis 241; and when tightened, locks axle 240 relative to both of these motions. In another such embodiment, set screw 539 provides gross Z-axis positioning capability, and screw knob 532 provides fine Z-axis positioning capability.

Figure 6A:
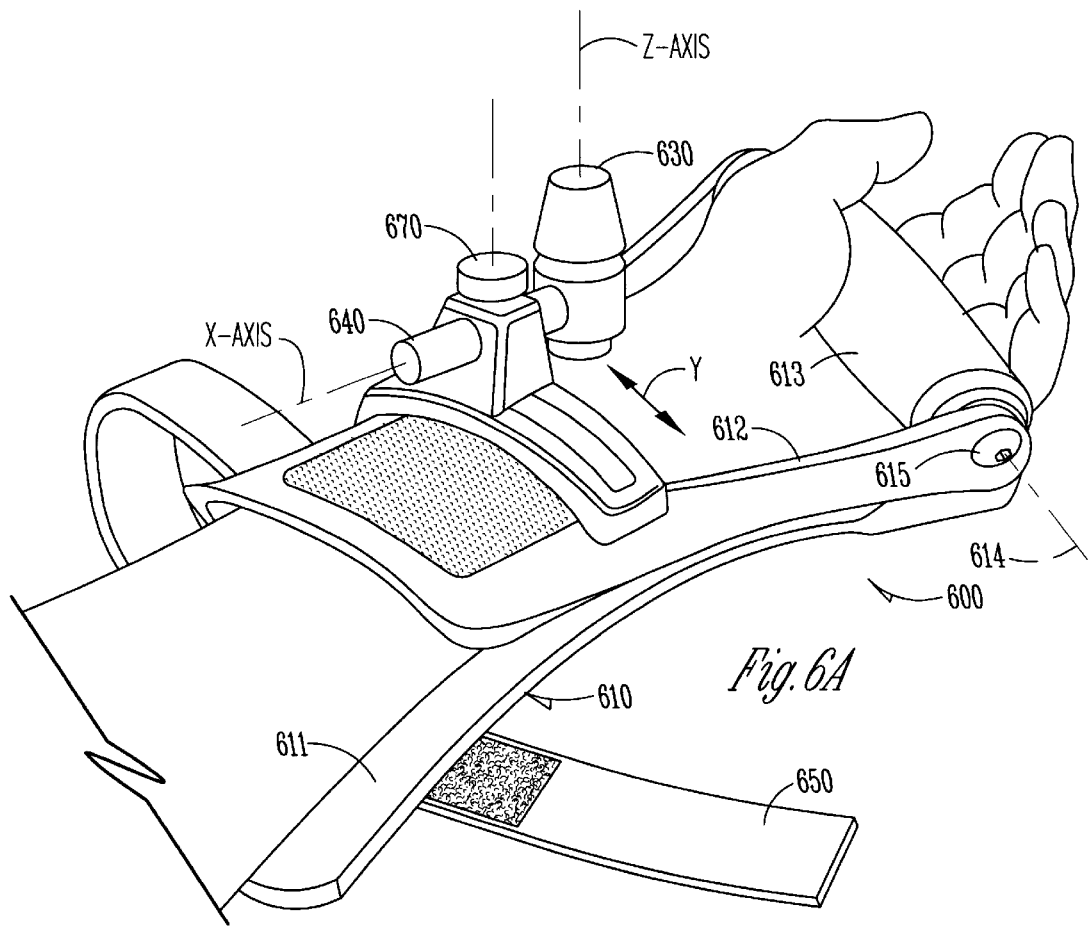
FIG. 6A shows an isometric view of one embodiment of sensor holder and wrist stabilizer 600 according to the present invention.
Figure 6B:
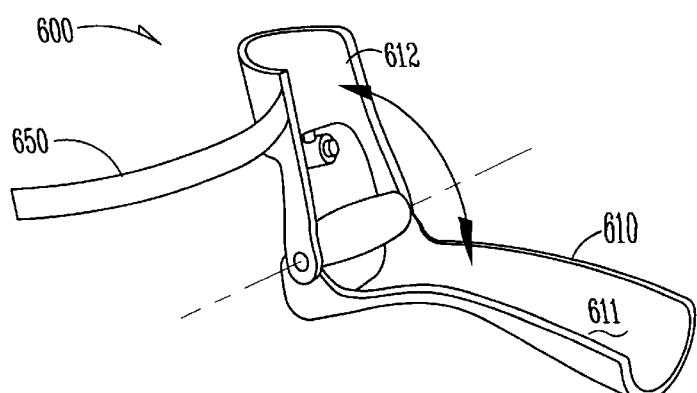
FIG. 6B shows another isometric view of one embodiment of sensor holder and wrist stabilizer 600 according to the present invention.

FIG. 6A shows an isometric view of one embodiment of sensor holder and wrist stabilizer 600 according to the present invention, wherein the functions of sensor holding and positioning device 300 are combined with the functions of wrist stabilizer 110. FIG. 6B shows another isometric view of this embodiment of sensor holder and wrist stabilizer 600. In this embodiment, wrist stabilizer 610 has a two-part clam-shell arrangement having back (or dorsal forearm) portion 611 attached to front (or anterior forearm) portion 612 using axle 615, and opening about axis 614. Palm grip 613 hold the palm in a similar manner as palm pad 115 of FIG. 1A. The Y-axis can be adjusted by sliding along slot mechanism 650. The X-axis can be adjusted by adjusting locking knob mechanism 670. The Z-axis can be adjusted by height-adjusting knob 630. Strap 650 hold the clam shell 610 together and in place.

Figure 7:
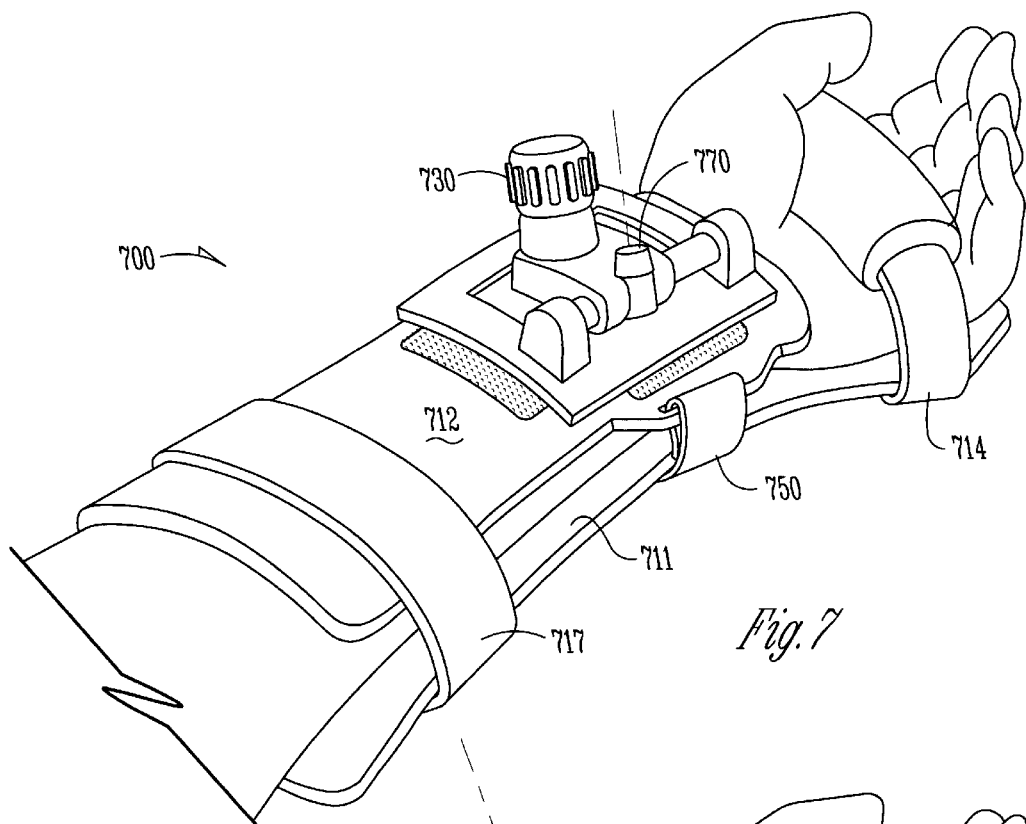
FIG. 7 shows an isometric view of one embodiment of sensor holder and wrist stabilizer 700 according to the present invention.

FIG. 7 shows an isometric view of another embodiment of sensor holder and wrist stabilizer 700 according to the present invention. Sensor holder and wrist stabilizer 700 is similar to sensor holder and wrist stabilizer 600 except the clam-shell arrangement hinges open along the radial aspect of the arm, and set-screw locking knob 770 provides both X-axis and Z-axis adjustment capability.

Figure 8:
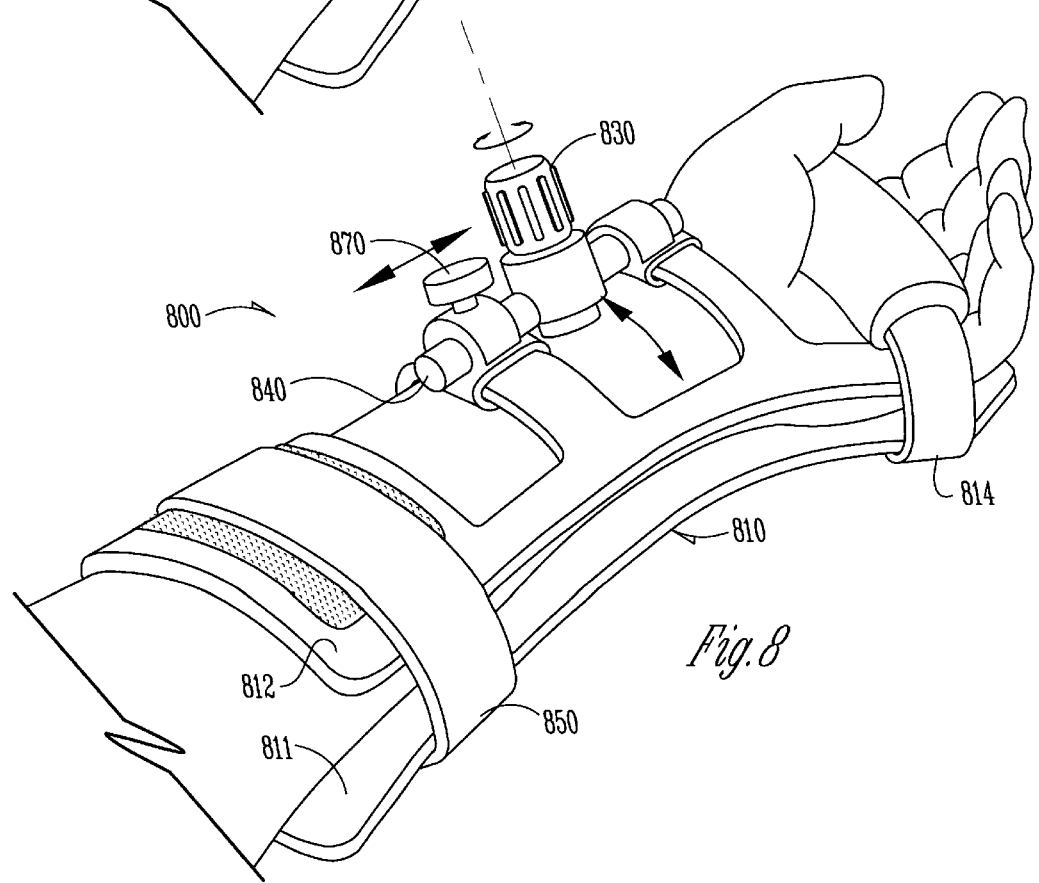
FIG. 8 shows an isometric view of one embodiment of sensor holder and wrist stabilizer 800 according to the present invention.

FIG. 8 shows an isometric view of one embodiment of sensor holder and wrist stabilizer 800 according to the present invention. Sensor holder and wrist stabilizer 800 is similar to sensor holder and wrist stabilizer 600 except the clam-shell arrangement hinges open along the radial aspect of the arm, and axle 840 is supported at both ends rather than being cantilevered as in FIG. 6A.

Figure 9:
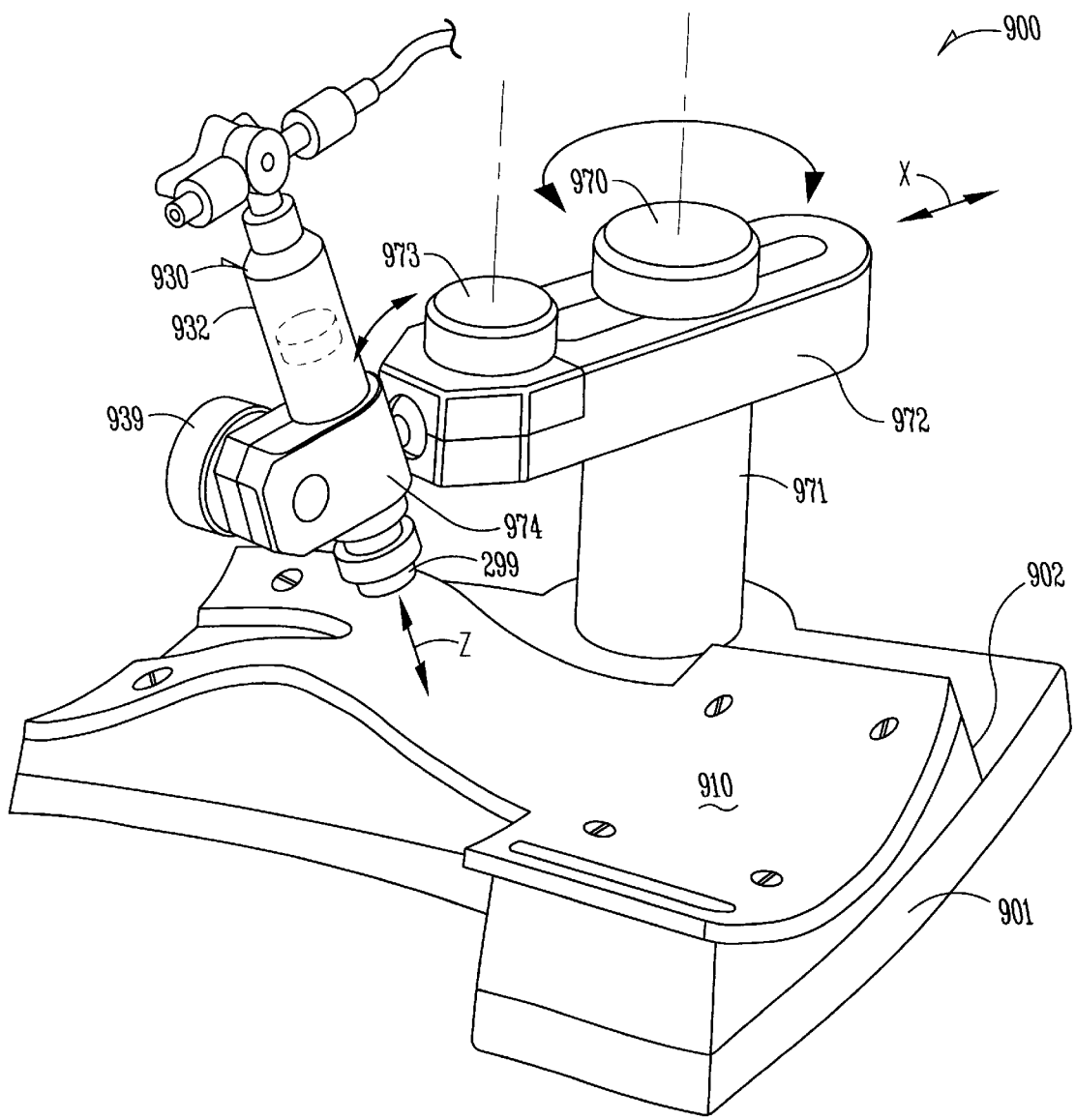
FIG. 9 shows an isometric view of one embodiment of sensor holder and wrist stabilizer 900 according to the present invention.

FIG. 9 shows an isometric view of one embodiment of sensor holder and wrist stabilizer 900 according to the present invention. Sensor holder and wrist stabilizer 900 is similar in overall function as the above sensor holder and wrist stabilizers 600, 700, and 800. Wrist stabilizer 910 provides the same function as wrist stabilizer 110 of FIGS. 1A–1D, but is attached to table support base plate 901 and cast urethane support 902. Post 971, slotted arm 972, and locking knob 970 that connects the two provide X and Y adjustment of the position of sensor 299. Ball- and socket joint 974 and its respective locking knob 973 provide a large amount of angular adjustment to the sensor. Locking knob 939 provides gross Z-axis adjustment, while syringe 932 provides fine Z-axis adjustment of hold-down pressure.

Configuration of Parts

Hold-Down Adjustment Knob/Screw Assembly 230: Threads provide smooth, low-friction, fine, hold-down adjustment. Knob 232 in one embodiment, is turned from 6061 aluminum metal alloy. The surface finish of knob in one embodiment, is parallel knurl. In one embodiment, a mark or line on the knob/screw assembly 230 is provided to allow the user to know how much they have turned the knob with each manual adjustment.

Sensor-holding-and-positioning device base 220: Width of opening between feet in footprint, in one embodiment, is 32 mm (1.28"). Length of footprint, in one embodiment, is no larger than approximately 55 mm (2.20"). The thumb side, in one embodiment, is clearly indicated on surface of frame with an adhesive label (or similar approach of marking). Pivot-arm holes raised 0.0625" higher than on an earlier prototype. Sensor-holder base 220 is to have pocket machined which will accept strain-relief 292 on cable/sensor assembly (G) (see: Minnesota Wire & Cable Co. (St. Paul, Minn.) part #SR KB-03, rev. A). Holes for attachment of end-caps, in one embodiment, is #6 tap size (diameter= 0.106"). Material, in one embodiment, is 6061 aluminum metal alloy. Surface finish, in one embodiment, is machined/ tumbled/anodized (clear).

Cushions 222: two identical parts assembly, each having 'd' shaped cross section, wherein the cross sections feature a 0.250" hole in center. They are manufactured by extrusion process. The material, in one embodiment, is Santoprene® 181-64, which is appropriate for skin contact in humans.

Pivot arm 240: it is attached to the sensor-holder base 220 in a manner that allows it to pivot and slide freely. It is able to align to a position normal (i.e., perpendicular) to the skin surface of patient's wrist. It slides longitudinally within frame to locate over "best" (i.e., strongest palpated) pulse location on radial artery. It does not have stops which limit rotation. It is held to frame with two identical endcaps 224. The lower side is counter-bored to a width of 0.550" and depth of 0.115". The inner threads, in one embodiment, are ½"–20 t.p.i. The material, in one embodiment, is 6061 aluminum metal alloy. The surface finish, in one embodiment, is machined/tumbled/anodized (clear).

Cable/sensor assembly (291 and 299): cable/sensor assembly, in one embodiment, is manufactured by Minnesota Wire & Cable Co. (St. Paul, Minn.). Arterial pulse pressure sensor 299 is supplied by Apollo Research Corporation, West Seneca, N.Y. (part #7013-52). Its height and configuration are designed to facilitate function of hold-down pressure adjustment. (See: the pulse pressure sensor as described in co-pending application entitled "SENSOR AND METHOD FOR SENSING ARTERIAL PULSE PRESSURE, filed on even date herewith and incorporated herein by reference). It swivels freely about the Z-axis of sensor suspension 230, to prevent twisting of cable when adjusting hold-down pressure, and prevent rubbing of skin when adjusting hold-down pressure. It is manufactured from medical-grade stainless steel. It is attached to knob/screw assembly of suspension 230 by #8-32 button-head hex screw (a). The strain relief 292 on cable assembly 291, in one embodiment, is Minnesota Wire & Cable Co. (St. Paul, Minn.) Part #SR KB-03. Cable 291, in one embodiment, is hard-wired directly to arterial pulse pressure sensor 299. Cable assembly specifications are any suitable cable specification well known in the art. Solutions Engineering, Inc., Stillwater, Minn., in one embodiment, provided suitable cable assembly specifications.

Endcaps 224: they are held to frame with #6-32 button-head hex screws 225. Their specific purpose is to prevent cushions 222 from sliding out of base unit 271, to capture strain-relief 292 on cable/sensor assembly 291 against slot 229, and to capture pivot arm 240 against slot(s) 228. The material, in one embodiment, is 6061 aluminum metal alloy. The surface finish, in one embodiment, is machined/ tumbled/anodized. The color, in one embodiment, is clear anodized. There is easy assembly because of two identical parts.

Button-Head Hex Screws 225: Four are required for assembly. They secure endcaps 224 onto base unit 271.

Wrist-Strap Assembly 250: It has a length to accommodate as small as wrist of the 5th percentile female population to as large as the 95th percentile male population & wrist stabilizer. It also has a length to accommodate almost all human phenotypes (obese persons, thin persons, etc.). The material, in one embodiment, is 1" wide, medium-weight cut loop, sewn. The floating buckle 254 will hook onto the post 227 of base unit 271 while strap is pulled through and removably attached to itself using medium-weight hook material. The end of strap, opposite end as frame, has a D-Ring sewn on which will prevent the loss of the floating buckle and provide a grip for the user. The end of strap 250, attached to base unit 271 through slot 226, has a loop sewn in. A drill rod 252 (length 1.25", φ=0.125") inserted into the loop prevents the strap from being pulled through the slot 226 from which it emerges. The sliding buckle 254 is sourced from ITW Nexus (Part #105-2100), color: Black. The sliding D-Ring is used to attach to post 227, and strap 250 slides through it to adjust length. The sewn D-Ring 256 is sourced from ITW Nexus (Part #412-1075) color: Black. The sewn D-ring can be grasped by the user to pull on strap 250. Hook-and-loop material 255 (see FIG. 2D) is used to attach strap 250 to itself once the strap 250 is adjusted through buckle 254 to the proper length or tightness.

The sensor holding and positioning device 200, includes a sensor-holder base 220 that holds a sensor 299 in a position overlying the radial artery on a patient's wrist.

In order to prevent the sensor-holder base 220 itself from substantially impeding the flow of blood through the radial artery, which would adversely affect the accuracy of the blood-pressure waveform data collected by the sensor, the frame is elevated above the wrist by two spaced-apart cushions 222 located on either side of, and approximately parallel to, the radial artery. Additional clearance is gained by elevating the central area of the sensor-holder base 220.

It is important that the sensor 299 be positioned over the "best" (i.e., strongest palpated) pulse on the patient's radial artery. Once this location is determined, it may be marked on the patient's wrist with a water-soluble pen or similar marker device. The entire sensor holding and positioning device 200 is then placed on the patient's wrist so that the sensor 299 is directly over the mark on the patient's wrist. If the patient's strongest palpated pulse is situated more distally on the patient's wrist, the sensor (which resides within the pivot arm 240) can be slid longitudinally within the frame until it is over the strongest palpated pulse location.

The sensor 299 must also be oriented approximately perpendicular to the surface of the patient's wrist and pressed against the wrist with a certain amount of force (hold-down pressure). Alignment perpendicular to the patient's wrist is achieved with the pivot arm 240. The pivot arm 240 freely rotates when the sensor 299 is not against the patient's wrist. Once the sensor 299 comes into contact with the patient's wrist, it stays oriented in a position which is approximately perpendicular to the surface of the patient's wrist. Hold-down pressure is achieved by tightening the knob/screw assembly 230. The threads on the knob/screw assembly 230 allow the sensor 299 to be raised or lowered at a preferred rate of 5 revolutions=0.250". The sensor 299 is attached to the knob/screw assembly 230 in a manner which allows it to swivel freely (prevents the cord from being twisted when hold-down pressure is being adjusted and also prevents the sensor from chafing against the patient's skin during hold-down pressure adjustment). Proper hold-down pressure (as well as proper location) of the sensor 299 is confirmed by observing a correct blood-pressure waveform pattern on the display screen. If the blood-pressure waveform is incorrect, it is necessary to alter hold-down pressure, alter position, or both.

The assembly is secured to the patient's wrist with a hook-and-loop adjustable strap which wraps around the patient's wrist and the wrist stabilizer 110 (which immobilizes the patient's wrist as well as holds it in the correct orientation). To accommodate quick attachment and detachment, a "floating" buckle 254 on strap 250 is attached to the post (which is machined into the frame), the strap pulled through taut, and finally attached back onto itself with hook-and-loop fastener material.

The end-caps 224 serve several purposes: to hold strap 250 in place, to hold pivot arm 240 in place, to hold strain-relief 292 in place, to hold cushions 222 in place, and to finish off the aesthetic form of sensor-holder base 220.

The cushions 222, which are formed by an extrusion manufacturing process, are designed to slip into the frame with a dove-tail configuration on their upper half. The lower half includes a "D" shape with a 0.250" diameter hole running through the center of the extrusion. This hole in the extrusion serves two purposes: (1) it minimizes the amount of shrink in the rubber material by creating a wall thickness which is more uniform; and (2) it makes the cushion feel softer against the skin surface of the patient's wrist. The material which was selected for the cushions was a U.S.P. CLASS VI extruding resin (color: black) which was soft enough in durometer to grip the skin of the patient, yet hard enough to be extruded within tolerance and also retained within the frame base unit 271.

Terminology

As used herein, the following terms are to have the respective following meanings.

A "sensor base" includes everything that holds the sensor suspension over the artery. A sensor base can be made of one or more pieces.

A "sensor suspension" is mounted to the sensor base in order to be held over the artery, and to position a sensor onto the artery. A sensor suspension can be made of one or more pieces.

A "sensor holder" is held by or is part of the sensor suspension and includes a member movable on z-axis to move the sensor up and down.

CONCLUSION

The purpose of the wrist sensor holding and positioning device 200 (the following discussion also applies to sensor holding and positioning devices 300, 400, 500, 600, 700, 800, and 900) and/or wrist stabilizers (i.e., 110, but also applies to 610, 710, 810, and 910) described above is to carefully and accurately situate an arterial pulse-pressure sensor 299 upon the skin overlying a patient's radial artery with the correct hold-down pressure. The intent of this is to obtain an arterial pulse pressure waveform which can then be analyzed by computer hardware and/or software, for example, in a Cardio Vascular Profiling Instrument as described in co-pending application "APPARATUS AND METHOD FOR BLOOD PRESSURE PULSE WAVEFORM CONTOUR ANALYSIS" filed on even date herewith and incorporated herein by reference.

If the arterial pulse pressure sensor 299 is not correctly situated upon the skin overlying a patient's radial artery, and/or the hold-down pressure is not correct, an improper blood-pressure waveform may be collected, thus affecting the accuracy and clinical value of the cardiovascular-profiling test.

The wrist sensor holding and positioning device, in one embodiment, is used in combination with a wrist stabilizer, which immobilizes the patient's wrist and holds it in proper orientation, so that the radial artery is closer to the skin surface and is stabilized for sensing.

In the preferred embodiments, the design of wrist stabilizer 110 allows palpation to be done with up to 3 fingers of the healthcare professional 88. In one embodiment, this is accomplished by removing the wrist sensor holding and positioning device 200 from the patient's wrist during palpation, and placing a small mark on the skin to highlight the optimal position for sensing as determined by palpation.

In the preferred embodiments, the design of wrist stabilizer 110 allows palpation to be done from either side of wrist. If necessary, this may be accomplished by removing the wrist sensor holding and positioning device from the patient's wrist during palpation.

In the preferred embodiments, the design of wrist sensor holding and positioning device easily accommodates the right or left wrist of patient.

The use of a water-soluble pen to mark the optimum arterial pulse pressure sensor placement location (determined by the healthcare professional by palpating the patient's radial artery) upon the patient's wrist is acceptable.

The wrist sensor holding and positioning device, in one embodiment, is attached to patient's wrist by healthcare professional after palpation.

In one embodiment, the X and Y location of arterial pulse pressure sensor is accommodated by moving the entire frame wrist sensor holding and positioning device to the appropriate location on patient's wrist. Additional Y adjustment is available by sliding the pivot arm longitudinally within the frame of the wrist sensor holding and positioning device. Additional X adjustment is available by pivoting sensor tangentially around the axis of the pivot arm 240.

Wrist sensor holding and positioning device 200 is configured to allow pivot arm 240 to rotate freely. When sensor 299 is tightened down against the skin, pivot arm 240 rotates to a position that orients the arterial pulse pressure sensor 299 somewhat more perpendicular to (i.e., normal to) the surface of the patient's wrist, and to the longitudinal axis of the underlying radial artery.

Hold-down pressure (travel in z-axis, perpendicular to or normal to the surface of patient's wrist) is adjusted by either tightening or loosening the hold-down knob/screw assembly.

Hold-down pressure adjustment, in one embodiment, is smooth (no indexes or "clicks"). In other embodiments, indexes that provide tactically-detectable "clicks" are provided. Further, in one embodiment, a mark on the knob/screw assembly 230 is provided to allow the user to know how much they have turned the knob with each adjustment.

It is understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A sensor holding and positioning device, comprising:
   a sensor base having at least two feet, the base forming a raised bridge between the two feet, the bridge having one or more cross members spanning all or part of the space between the two feet, wherein the two feet are positioned on either side of an area to be sensed such that the space between the feet is over the area to be sensed;

a sensor suspension including a sensor holder and sensor-height-adjustment mechanism; and a pivot-arm axle having a long axis, the axle coupled to and between the sensor suspension and the sensor base such that the sensor suspension is able to rotate in an arc about the long axis of the axle over the area to be sensed.

2. The device according to claim 1, further comprising a pressure sensor attached to the sensor holder of the sensor suspension.

3. The device according to claim 1, wherein the axle is also coupled to and between the sensor suspension and the sensor base such that the sensor suspension is able to slide back and forth along a line parallel to a line that extends through the space between the two feet but that does not intersect either of the two feet.

4. The device according to claim 1, wherein the two feet are each elongate and substantially parallel to one another.

5. The device according to claim 1, wherein the two feet are each elongate and substantially parallel to one another, and wherein the axle is also coupled to and between the sensor suspension and the sensor base such that the sensor suspension is able to slide back and forth along a line that is generally parallel to the long axis of the axle and parallel to the two feet.

6. The device according to claim 1, wherein the axle is rotatably coupled to the sensor base such that the long axis of the axle can be rotated about a point on the long axis and thus positioned to each of two or more angular positions.

7. The device according to claim 1, further comprising:

a wrist stabilizer, the stabilizer comprising a first member shaped on a forearm portion to conform to contours of a forearm, shaped on a wrist portion to contours of a wrist, and shaped on a hand portion to the contours of a hand, and forming an angle of approximately 150 degrees between the forearm portion and the hand portion, the stabilizer further including one or more straps for holding the forearm to the stabilizer.

8. The device according to claim 7, further comprising a pressure sensor attached to the sensor holder of the sensor suspension.

9. The device according to claim 7, wherein the stabilizer includes a second member that holds a portion of a patient's fingers in an extended position.

10. The device according to claim 7, wherein the stabilizer includes a strap that is positionable to hold a portion of a patient's fingers in an extended position.

11. The device according to claim 7, wherein the stabilizer includes one or more straps for holding the hand to the stabilizer.

12. The device according to claim 1, further comprising a pressure sensor attached to the sensor holder of the sensor suspension, and wherein the two feet are each elongate and substantially parallel to one another, the axle is also coupled to and between the sensor suspension and the sensor base such that the sensor suspension is able to slide back and forth along a line that is generally parallel to the artery and generally parallel to and between the two feet, and the axle is rotatably coupled to the sensor base such that the long axis of the axle can be rotated about a point on the long axis and thus positioned to each of two or more angular positions.

13. The device according to claim 1, further comprising a pressure sensor attached to the sensor holder of the sensor suspension, and wherein the two feet are each elongate and substantially parallel to one another, the bridge includes two cross members spanning the space between the two feet, the axle is also coupled to and between the two cross members such that the sensor is able to be slid back and forth to each of two or more linear positions between the two cross members along a line that is generally parallel to the artery and generally parallel to and between the two feet, and the axle is rotatably coupled to the two cross members such that the long axis of the axle can be rotated about a point on the long axis and thus positioned to each of two or more angular positions.

14. The device according to claim 1, wherein the sensor suspension includes a manually rotatable screw height-adjustment mechanism.

15. The device according to claim 1, further comprising a pressure sensor attached to the sensor holder of the sensor suspension, and wherein the sensor suspension includes a manually rotatable screw height-adjustment mechanism, the two feet are each elongate and substantially parallel to one another, the axle is also coupled to and between the sensor suspension and the sensor base such that the sensor suspension is able to slide back and forth along a line that is generally parallel to the artery and generally parallel to and between the two feet, and the axle is rotatably coupled to the sensor base such that the long axis of the axle can be rotated about a point on the long axis and thus positioned to each of two or more angular positions.

16. The device according to claim 1, further comprising a pressure sensor attached to the sensor holder of the sensor suspension, and wherein the sensor suspension includes a manually rotatable screw height-adjustment mechanism, the two feet are each elongate and substantially parallel to one another, the bridge includes two cross members spanning the space between the two feet, the axle is also coupled to and between the two cross members such that the sensor is able to be slid back and forth to each of two or more linear positions between the two cross members along a line that is generally parallel to the artery and generally parallel to and between the two feet, and the axle is rotatably coupled to the two cross members such that the long axis of the axle can be rotated about a point on the long axis and thus the sensor can be positioned to each of two or more angular positions.

17. The device according to claim 1, further comprising a pressure sensor attached to the sensor holder of the sensor suspension, and wherein the two feet are each elongate and substantially parallel to one another.

18. The device according to claim 1, further comprising a pressure sensor attached to the sensor holder of the sensor suspension, and wherein the two feet are each elongate and substantially parallel to one another, and the axle is also coupled to and between the sensor suspension and the sensor base such that the sensor suspension is able to slide back and forth along a line that is generally parallel to the long axis of the axle and parallel to the two feet.

19. The device according to claim 1, further comprising a pressure sensor attached to the sensor holder of the sensor suspension, and wherein the axle is rotatably coupled to the sensor base such that the long axis of the axle can be rotated about a point on the long axis and thus positioned to each of two or more angular positions.

20. The device according to claim 1, further comprising a pressure sensor attached to the sensor holder of the sensor suspension, and wherein the sensor suspension holds the sensor in a linearly and rotatably adjustable position beside one or more feet of the sensor base, whereby the sensor may positioned at a desired location and angle on a subject's body.

21. A sensor holding and positioning device, comprising:
- a sensor base having at least two feet, the base forming a raised bridge between the two feet, the bridge having one or more cross members spanning the space between the two feet, wherein the two feet are positioned on either side of an area to be sensed such that the space between the feet is over the area to be sensed;
- a sensor suspension including a sensor holder and sensor-height-adjustment mechanism;
- a pivot-arm axle having a long axis, the axle coupled to and between the sensor suspension and the sensor base such that the sensor suspension is able to rotate in an arc about the long axis of the axle over the area to be sensed; and
- a pressure sensor attached to the sensor holder of the sensor suspension, wherein the axle is also coupled to and between the sensor suspension and the sensor base such that the sensor suspension is able to slide back and forth along a line parallel to the long axis of the axle.

22. A sensor holding and positioning device, comprising:
- a sensor base having at least two feet, the base forming a raised bridge between the two feet, the bridge having one or more cross members spanning the space between the two feet, wherein the two feet are positioned on either side of an area to be sensed such that the space between the feet is over the area to be sensed;
- a sensor suspension including a sensor holder and sensor-height-adjustment mechanism;
- a pivot-arm axle having a long axis, the axle coupled to and between the sensor suspension and the sensor base such that the sensor suspension is able to rotate in an arc about the long axis of the axle over the area to be sensed; and
- a pressure sensor attached to the sensor holder of the sensor suspension, and wherein the axle is also coupled to and between the sensor suspension and the sensor base such that the sensor is able to be slid back and forth along a line generally parallel to a perpendicular bisector of a line connecting the two feet.

* * * * *